(12) United States Patent
Meinhold et al.

(10) Patent No.: US 12,262,956 B2
(45) Date of Patent: Apr. 1, 2025

(54) SYSTEMS AND METHODS FOR MAGNETIC RESONANCE IMAGING GUIDED ROBOTICS

(71) Applicants: Georgia Tech Research Corporation, Atlanta, GA (US); Emory University, Atlanta, GA (US)

(72) Inventors: Waiman Meinhold, Atlanta, GA (US); Ai-Ping Hu, Atlanta, GA (US); John N. Oshinski, Atlanta, GA (US); Jun Ueda, Atlanta, GA (US); Daniel E. Martinez, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 668 days.

(21) Appl. No.: 17/404,619

(22) Filed: Aug. 17, 2021

(65) Prior Publication Data
US 2022/0047334 A1    Feb. 17, 2022

Related U.S. Application Data

(60) Provisional application No. 63/066,578, filed on Aug. 17, 2020.

(51) Int. Cl.
| | | |
|---|---|---|
| *A61B 5/00* | (2006.01) | |
| *A61B 34/20* | (2016.01) | |
| *A61B 34/30* | (2016.01) | |
| *A61M 5/42* | (2006.01) | |
| *B25J 9/16* | (2006.01) | |
| *G01R 33/28* | (2006.01) | |
| *A61B 90/00* | (2016.01) | |

(52) U.S. Cl.
CPC ............. *A61B 34/20* (2016.02); *A61B 34/30* (2016.02); *A61M 5/427* (2013.01); *B25J 9/1694* (2013.01); *G01R 33/287* (2013.01); *A61B 2034/2051* (2016.02); *A61B 2090/3954* (2016.02)

(58) Field of Classification Search
CPC ...... A61B 2034/2046; A61B 2034/107; A61B 2034/301; A61B 90/11; G01R 33/285
See application file for complete search history.

(56) References Cited

U.S. PATENT DOCUMENTS

| | | | | |
|---|---|---|---|---|
| 6,088,488 A | * | 7/2000 | Hardy | A61B 6/464 382/130 |
| 2013/0274596 A1 | * | 10/2013 | Azizian | A61B 34/30 600/424 |
| 2013/0345718 A1 | * | 12/2013 | Crawford | A61B 90/39 606/130 |
| 2014/0058406 A1 | * | 2/2014 | Tsekos | A61B 34/30 606/130 |
| 2016/0249990 A1 | * | 9/2016 | Glozman | A61B 34/30 606/130 |
| 2016/0349335 A1 | * | 12/2016 | Olsen | G01R 33/286 |

\* cited by examiner

*Primary Examiner* — Rajeev P Siripurapu
(74) *Attorney, Agent, or Firm* — Troutman Pepper Locke LLP; Ryan A. Schneider; Andrew C. Doherty

(57) ABSTRACT

An exemplary embodiment of the present disclosure provides an MRI-compatible robot comprising one or more fiducial markers, a first planar stage comprising a first joint configured to receive a surgical tool and a first mechanism configured to move the surgical tool, a second planar stage comprising a second joint configured to receive the surgical tool and a second mechanism configured to move the surgical tool, and wherein the second planar stage is generally parallel with the first planar stage.

12 Claims, 23 Drawing Sheets

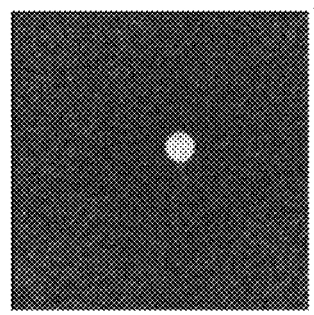 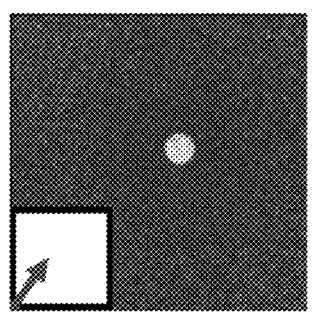
FIG. 19A  FIG. 19B
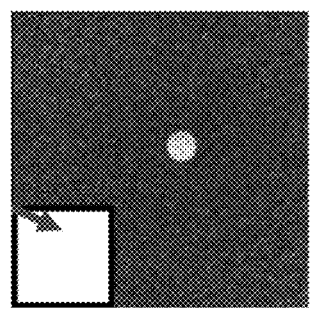 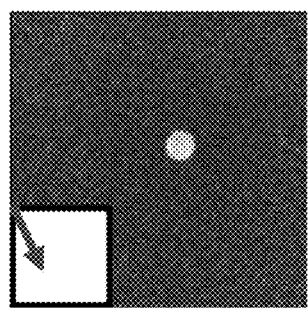
FIG. 19C  FIG. 19D
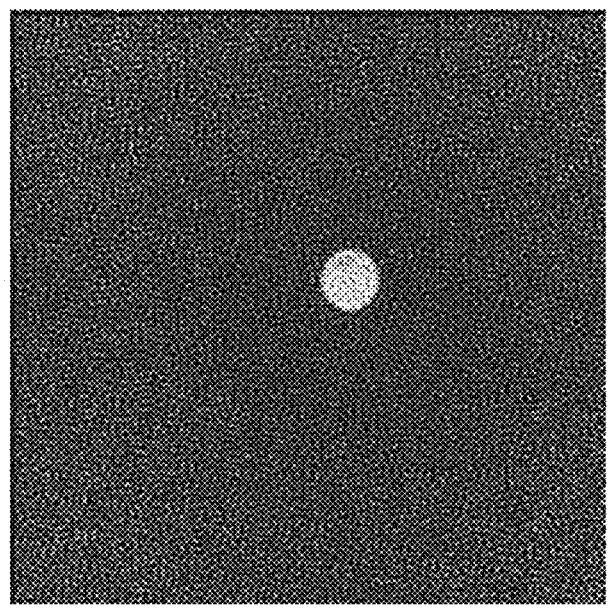
FIG. 19E

FIG. 20A  FIG. 20B

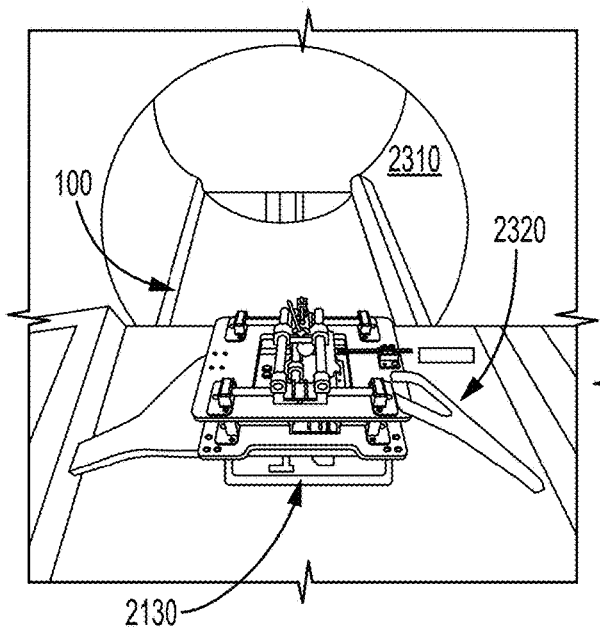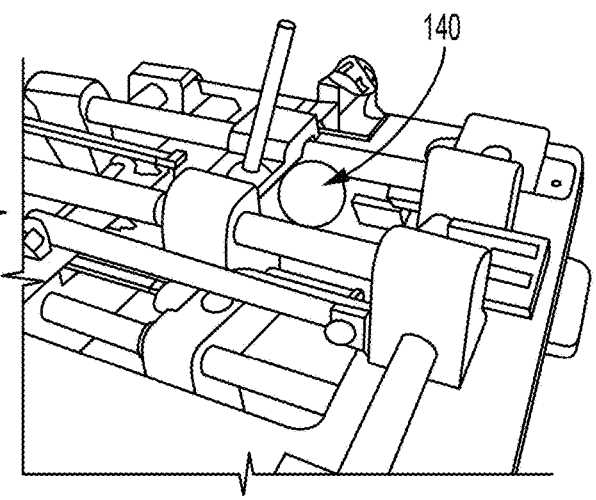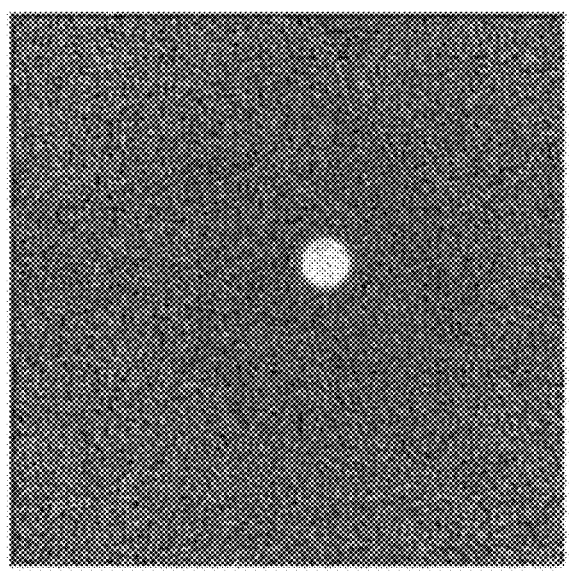
FIG. 23A
FIG. 23B
FIG. 23C

SYSTEMS AND METHODS FOR MAGNETIC RESONANCE IMAGING GUIDED ROBOTICS

CROSS-REFERENCE TO RELATED APPLICATIONS

This application claims the benefit of U.S. Provisional Application Ser. No. 63/066,578 filed on Aug. 17, 2020, which is incorporated herein by reference in its entirety as if fully set forth below.

GOVERNMENT LICENSE RIGHTS

This invention was made with government support under 1662029 and 1545287 awarded by the National Science Foundation. The government has certain rights in the invention.

FIELD OF THE DISCLOSURE

The present disclosure relates generally to health systems and methods and more particularly to a systems and methods for magnetic resonance imaging (MRI) guided robotics.

BACKGROUND

Recent developments in the field of cellular therapeutics have indicated the potential of stem cell injections directly to the spinal cord. This injection procedure allows for direct delivery of cellular therapeutics, avoiding the need for diffusion. The targeted area is very small, with a narrow trajectory necessary to avoid vertebrae and other sensitive tissues. The current procedure involves either open surgery or a Magnetic Resonance Imaging (MRI) based minimally invasive version. The minimally invasive MRI based procedure is preferable to mitigate the damage that occurs during open surgery. However, needle positioning during MRI imaging remains a significant hurdle. Clinicians can adjust the needle positioning based on the MRI imaging, but this requires the patient be removed from the MRI machine each time the needle position is adjusted. For example, the patient is removed, the device is adjusted to move the needle point closer to the target pose, and then the patient is re-inserted and re-imaged. This process is repeated multiple times before final needle delivery, such that on average the patient insert-remove iterations add upwards of 90 minutes (about one-quarter of the total time) to the cell injection procedure. Therefore, what is needed to improve both the speed and accuracy of this procedure, is an MRI compatible robotic needle positioning system.

SUMMARY

The present disclosure relates to health systems and methods. The disclosed technology includes an MRI-compatible surgical robot. The robot can include one or more fiducial markers, a first planar stage, and a second planar stage. The first planar stage can include a first joint and a first mechanism. The first joint can be configured to receive a surgical tool. The first mechanism can be configured to move the surgical tool. The second planar stage can include a second joint and a second mechanism. The second joint can be configured to receive the surgical tool. The second mechanism can be configured to move the surgical tool. The second planar stage can be generally parallel with the first planar stage.

The first mechanism and second mechanism can include direct drive linear actuators.

The first mechanism and second mechanism can include piezoelectric actuators.

The first mechanism can include a first x-axis actuator and a first y-axis actuator. The first x-axis actuator can be generally perpendicular to the first y-axis actuator. The second mechanism can include a second x-axis actuator and a second y-axis actuator. The second x-axis actuator can be generally perpendicular to the second y-axis actuator.

The first x-axis actuator and the first y-axis actuator can be configured to move the first joint. The second x-axis actuator and the second y-axis actuator can be configured to move the second joint. The first joint can be configured to receive a proximal portion of the surgical tool. The second joint can be configured to receive a distal portion of the surgical tool. The first joint can be configured to allow the proximal portion of the surgical tool to move with two degrees of freedom. The second joint can be configured to allow the distal portion of the surgical tool to move with two degrees of freedom. The first joint and second joint can be configured to move independently to allow the surgical tool to move with four degrees of freedom.

The first joint and second joint can be ball joints.

The first joint can be configured to be a free fit with respect to the surgical tool. The second joint can be configured to be a press fit with respect to the surgical tool.

The one or more fiducial markers can include a first fiducial marker and a second fiducial marker. The first fiducial marker can be configured to reflect a position of the first mechanism. The second fiducial marker can be configured to reflect a position of the second mechanism.

The one or more fiducial markers can include a first fiducial marker coaxial with a proximal portion of the surgical tool. The one or more fiducial markers can include a second fiducial marker coaxial with a distal portion of the surgical tool.

The surgical tool can include a cannula. The cannula can be configured to extend through the first and second joints.

The surgical tool can include a needle. The needle can be configured to be inserted into the cannula. The needle can be configured to inject a substance into a patient.

The robot can be configured to allow a user can control a depth of the needle into the patient.

The robot can include a controller. The controller can be configured to move, by the first and second mechanisms, the surgical tool to a target location based, at least in part, on visual servoing.

The one or more fiducial markers can include an MRI-visible substance. The one or more fiducial markers can be symmetrical and coaxial with a line between the first joint and the second joint.

The disclosed technology includes a method of controlling a robot. The method for controlling a robot can include receiving, by a controller, target fiducial coordinates indicative of a desired position of one or more fiducial markers of a surgical tool. The method for controlling a robot can include receiving, by a controller, an MRI image, from an Mill machine. The MRI image can include a position of the one or more fiducial markers of the surgical tool. The method for controlling a robot can include determining a fiducial position error based, at least in part, on the position of the one or more fiducial markers of the surgical tool in the MRI image and the target fiducial coordinates. The method for controlling a robot can include moving, by one or more actuators of the robot, the surgical tool to a position based, at least in part, on the fiducial position error.

The method for controlling a robot can include repeating steps to drive the fiducial position error towards zero. The repeating can include repeating the steps of: receiving, by a controller, an image, from an MM machine, comprising the position of the one or more fiducial markers of the surgical tool; determining a fiducial position error based on the position of the one or more fiducial markers of the surgical tool in the MM image and the target fiducial coordinates; and moving, by one or more actuators of the robot, the surgical tool to a position based, at least in part, on the determined fiducial position error. The method for controlling a robot can include determining that the position of the one or more fiducial markers of the surgical tool in the MM image is coincident with the target fiducial coordinates.

The method for controlling a robot can include visual servoing.

The method for controlling a robot can include receiving, by the controller, a plurality of images, from an MRI machine, comprising the position of the one or more fiducial markers of the surgical tool. The method for controlling a robot can include merging the plurality of images. The method for controlling a robot can include estimating a higher resolution image comprising the position of the one or more fiducial markers of the surgical tool, based, at least in part, on the merged plurality of images.

The plurality of images can be spatially shifted images wherein each of the plurality of images is spatially shifted by a known amount.

The method for controlling a robot can include determining, prior to performing the method of: receiving, by the controller, a plurality of images, from an MRI machine, comprising the position of the one or more fiducial markers of the surgical tool; merging the plurality of images; and estimating a higher resolution image comprising the position of the one or more fiducial markers of the surgical tool, based, at least in part, on the merged plurality of images, that the position of the one or more fiducial markers of the surgical tool in the MRI image is coincident with the target fiducial coordinates.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features can also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 19A provides an image with no spatial shift, in accordance with the present disclosure.

FIG. 19B provides a spatially shifted image, in accordance with the present disclosure.

FIG. 19C provides a spatially shifted image, in accordance with the present disclosure.

FIG. 19D provides a spatially shifted image, in accordance with the present disclosure.

FIG. 19E provides a reconstructed image, in accordance with the present disclosure.

FIG. 20A provides a graph of estimated against true center point positions, in accordance with the present disclosure.

FIG. 20B provides a graph of estimated against true center point positions, in accordance with the present disclosure.

FIG. 23A provides a photo of an experimental setup, in accordance with the present disclosure.

FIG. 23B provides a photo of a surgical robot, in accordance with the present disclosure.

FIG. 23C provides a resolution enhanced image, in accordance with the present disclosure.

DETAILED DESCRIPTION

Figure 1:
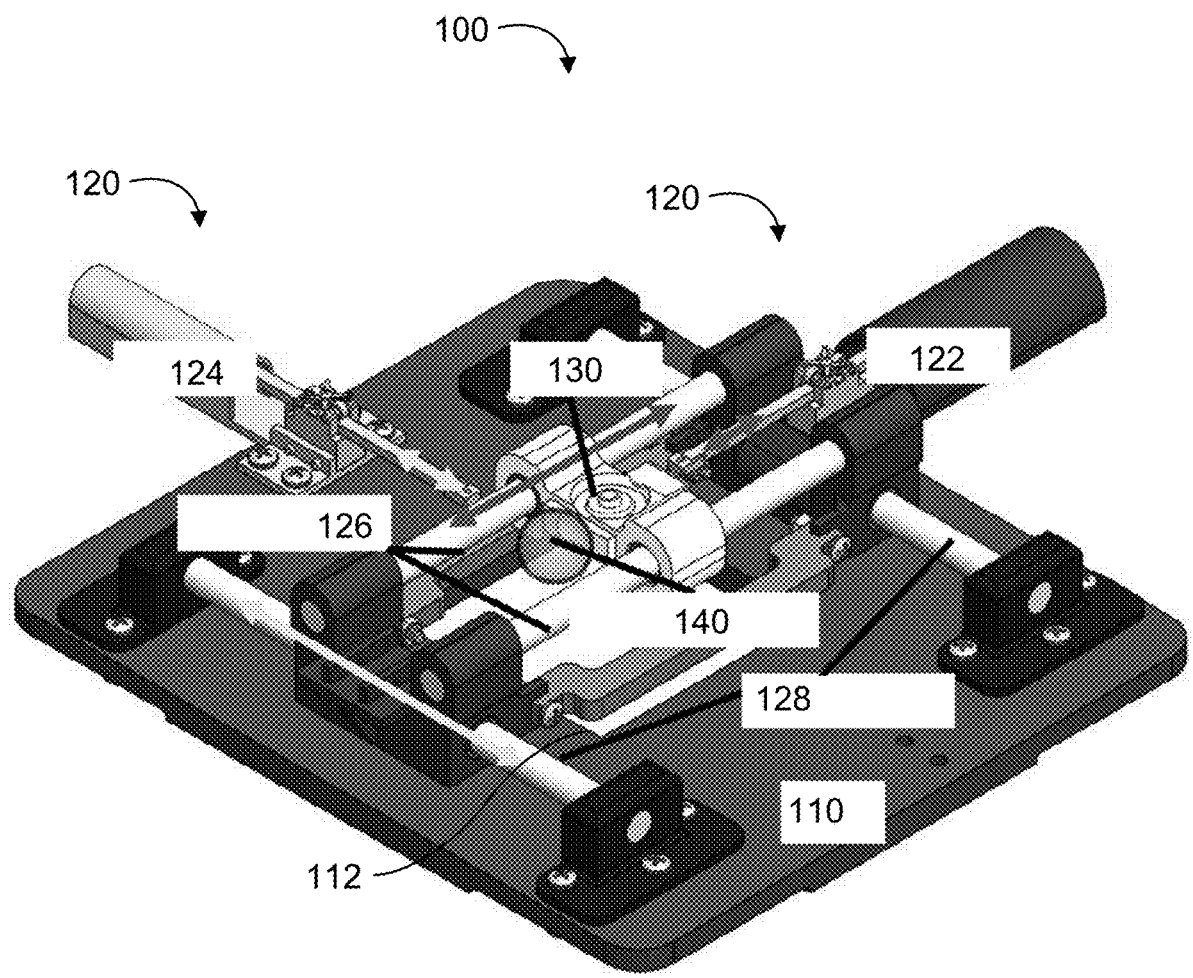
FIG. 1 provides a surgical robot, in accordance with the present disclosure.

Throughout this disclosure we describe systems and methods for MM-guided robotics. For example, a system and method to control the robot based, at least in part, on MRI imaging. The robot can be a needle-positioning robot that can precisely and quickly position a needle in the spine of a patient.

While the disclosed technology is described throughout this disclosure in relation to a system for positioning a needle for spinal injections during an MM, those having skill in the art will recognize that the disclosed technology is not so limited and can be applicable to other scenarios and applications. For example, it is contemplated that the disclosed technology can be applicable to any application that requires a surgical tool be precisely and quickly positioned based, at least in part, on MRI imaging. This can include precisely positioning a needle, or other surgical tool, at locations of the body other than the spine. Additionally, it is contemplated that the disclosed technology can be applicable to any precision application, including, but not limited to, precision surgery, minimally-invasive surgery, robotic surgery, or other robotic applications, both inside and out of an MRI machine.

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Indeed, it is to be understood that other examples are contemplated. Many suitable components that would perform the same or similar functions as components described herein are intended to be embraced within the scope of the disclosed electronic devices and methods. Such other components not described herein may include, but are not limited to, for example, components developed after development of the disclosed technology.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified. Further, it is contemplated that the disclosed methods and processes can include, but do not necessarily include, all steps discussed herein. That is, methods and processes in accordance with the disclosed technology can include some of the disclosed while omitting others.

Throughout the specification and the claims, the following terms take at least the meanings explicitly associated herein, unless otherwise indicated. The term "or" is intended to mean an inclusive "or." Further, the terms "a," "an," and "the" are intended to mean one or more unless specified otherwise or clear from the context to be directed to a singular form. By "comprising," "containing," or "including" it is meant that at least the named element, or method step is present in article or method, but does not exclude the presence of other elements or method steps, even if the other such elements or method steps have the same function as what is named.

As used herein, unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Although the disclosed technology may be described herein with respect to various systems and methods, it is contemplated that embodiments or implementations of the disclosed technology with identical or substantially similar features may alternatively be implemented as methods or systems. For example, any aspects, elements, features, or the like described herein with respect to a method can be equally attributable to a system. As another example, any aspects, elements, features, or the like described herein with respect to a system can be equally attributable to a method.

Reference will now be made in detail to examples of the disclosed technology, examples of which are illustrated in the accompanying drawings and disclosed herein. Wherever convenient, the same reference numbers will be used throughout the drawings to refer to the same or like parts.

Referring now to the drawings, in which like numerals represent like elements, examples of the present disclosure are herein described. As will be described in greater detail, the present disclosure can include a system and method to control a robot. To provide a background of the system described in the present disclosure, components of the system for a robot are shown in FIG. 1 and will be discussed first.

To facilitate an understanding of the principles and features of the present disclosure, various examples of the disclosed technology are explained herein. The components, steps, and materials described herein as making up various elements of the disclosed technology are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

As used herein, unless otherwise noted, the term "image" or "MRI image" refers to one or more images produced from magnetic resonance imaging. For example, image can refer to a three-dimensional scan which can comprise multiple individual images.

As used herein, unless otherwise noted, the term "surgical tool" refers to any tool, device, or structure that can be used in a medical procedure. For example, surgical tool can refer to a needle.

As shown in FIG. 1, the disclosed technology includes an MRI-compatible surgical robot 100. The robot 100 can include a first planar stage 110. The first planar stage 110 can include a solid, relatively flat and planar structure whereon a plurality of structures, devices, mechanisms, and the like, can be attached. For example, as illustrated in FIG. 1, the first planar stage 110 can have one or more fiducial markers, a first joint 130, and a first mechanism 120. The one or more fiducial markers can include a first fiducial marker 140. Alternatively, or in addition, the first joint 130 can be configured to receive a surgical tool 250. Additionally, the first planar stage 110 can include an opening. For example, the planar stage can have a first opening 112 near or at the geometric center of the first planar stage 110.

The first mechanism 120 can be configured to move the surgical tool 250. The first mechanism 120 can effectuate the movement the surgical tool by any movement method known in the art, including but not limited to, direct drive, pneumatic, hydraulic, serial manipulator, cable drive, gears, wheels, pulleys, rack and pinion, and the like, or any combination thereof. For example, the first mechanism 120 can include one or more direct-drive actuators. Alternatively, or in addition, the first mechanism 120 can include piezoelectric actuators. For example, the first mechanism 120 can include piezoelectric direct-drive actuators. Alternatively, or in addition, the first mechanism 120 can include a first x-axis actuator 122 and a first y-axis actuator 124. The first x-axis actuator 122 can be generally perpendicular to the first y-axis actuator 124.

The first mechanism 120 can include one or more guide rods. For example, the first mechanism 120 can include a first x-axis guide rod 126 and a first y-axis guide rod 128. Alternatively, or in addition, the first mechanism 120 can include one or more guide wires, pulleys, motors, gears, wheels, gear racks, rack and pinion, bearings, guide rails, winches, and the like, or any combination thereof. The first x-axis guide rod 126 can be generally perpendicular to the first y-axis guide rod 128. The first guide rods 126, 128 can include one or more rods. As illustrated in FIG. 1, the first guide rods 126, 128 can each include two rods that run parallel to one another. The first guide rods 126, 128 can be any low friction material, including, but not limited to, plastics, metals, polymers, resins, composites, and the like, or any combination thereof. For example, the first guide rods 126, 128 be made from acetal resin. The first guide rods 126, 128 can allow a structure to be slidably connected. For example, a structure can be slidably connected to the first guide rods 126, 128 by a sleeve bearing.

The first joint 130 can be configured to receive a surgical tool 250 and allow for the surgical tool 250 to move with at least one degree of freedom. For example, the first joint 130 can have a hole through which the surgical tool 250 can pass through. Alternatively, or in addition, the first joint 130 can have a hole through which a surgical tool guide can pass through. For example, a surgical tool guide can be a cannula which can guide a surgical tool. The first joint 130 can be any joint known in the art, including, but not limited, a ball joint, ball and socket joint, hinge joint, pivot joint, prismatic joint, and the like, or any combination thereof. For example, the first joint 130 can be a ball joint.

The first joint 130 can be connected to the first mechanism 120. For example, the first joint 130 can be slidably connected to the first guide rods 126, 128 of the first mechanism 120. As illustrated in FIG. 1, the first joint 130 can be slidably connected to the first x-axis guide rod 126. Alternatively, or in addition, the first x-axis guide rod 126 can be slidably connected to the first y-axis guide rod 128. For example, the first x-axis actuator 122 can actuate the first joint 130 to move along the first x-axis guide rod 126 and the first y-axis actuator 124 can actuate the first x-axis guide rod 126 to move along the first y-axis guide rod 128. The first mechanism 120 can thereby move the first joint 130 with two degrees of freedom.

Figure 2:
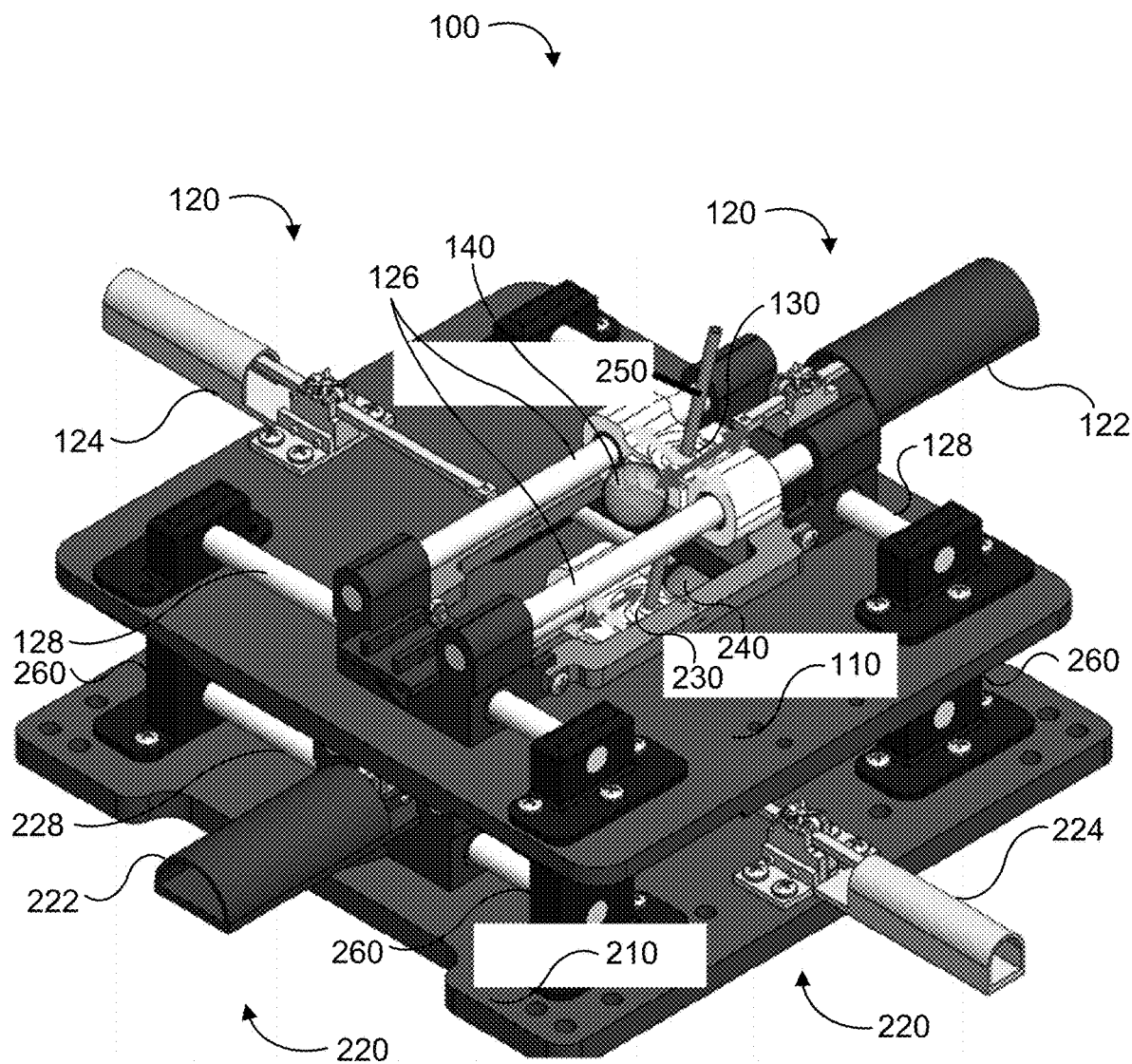
FIG. 2 provides a surgical robot, in accordance with the present disclosure.

As shown in FIG. 2, the robot 100 can include a first planar stage 110 and a second planar stage 210. The first planar stage 110 can be generally parallel to the second planar stage 210. Alternatively, or in addition, the first planar stage 110 and the second planar stage 210 can be connected. For example, the first planar stage 110 and the second planar stage 210 can be rigidly connected by one or more brackets 260. The brackets 260 can have a height, such that the first planar stage 110 and the second planar stage 210 are separated by that height. As illustrated in FIG. 2, the brackets 260 can be located at or near the four corners of the first planar stage 110 and the second planar stage 210.

The second planar stage 210 can include some or all of the features, structures, and mechanisms of the first planar stage 110. For example, the second planar stage can include a second mechanism 220 and a second joint 230. Alternatively, or in addition, the second planar stage can be configured largely the same as the first planar stage 110.

The robot 100 can include a second planar stage 210. The second planar stage 210 can include a solid, relatively flat and planar structure whereon a plurality of structures, devices, mechanisms, and the like, can be attached. For example, as illustrated in FIG. 2, the second planar stage 210 can have one or more fiducial markers, a second joint 230, and a second mechanism 220. The one or more fiducial markers can include a second fiducial marker 240. Alternatively, or in addition, the second joint 230 can be configured to receive a surgical tool 250. Additionally, the second planar stage 210 can include an opening. For example, the planar stage can have an opening near or at the geometric center of the second planar stage 210.

The second mechanism 220 can be configured to move the surgical tool 250. The second mechanism 220 can effectuate the movement the surgical tool by any movement method known in the art, including but not limited to, direct drive, pneumatic, hydraulic, serial manipulator, cable drive, gears, wheels, pulleys, rack and pinion, and the like, or any combination thereof. For example, the second mechanism 220 can include one or more direct-drive actuators. Alternatively, or in addition, the second mechanism 220 can include piezoelectric actuators. For example, the second mechanism 220 can include piezoelectric direct-drive actuators. Alternatively, or in addition, the second mechanism 220 can include a second x-axis actuator 222 and a second y-axis actuator 224. The second x-axis actuator 222 can be generally perpendicular to the second y-axis actuator 224.

The second mechanism 220 can include one or more guide rods. For example, the second mechanism 220 can include a second x-axis guide rod 226 (not shown) and a second y-axis guide rod 228. Alternatively, or in addition, the second mechanism can include one or more guide wires, pulleys, motors, gears, wheels, gear racks, rack and pinion, bearings, guide rails, winches, and the like, or any combination thereof. The second x-axis guide rod 226 can be generally perpendicular to the second y-axis guide rod 228. The second guide rods 226, 228 can include one or more rods. As illustrated in FIG. 1 with respect to the first guide rods 126, 128, the second guide rods 228, 226 can similarly each include two rods that run parallel to one another. The second guide rods 226, 228 can be any low friction material, including, but not limited to, plastics, metals, polymers, resins, composites, and the like, or any combination thereof. For example, the second guide rods 226, 228 be made from acetal resin. The second guide rods 226, 228 can allow a structure to be slidably connected. For example, a structure can be slidably connected to the second guide rods 226, 228 by a sleeve bearing.

The second joint 230 can be configured to receive a surgical tool 250 and allow for the surgical tool 250 to move with at least one degree of freedom. For example, the second joint 230 can have a hole through which the surgical tool 250 can pass through. Alternatively, or in addition, the second joint 230 can have a hole through which a surgical tool guide can pass through. For example, a surgical tool guide can be a cannula which can guide a surgical tool 250. The second joint 230 can be any joint known in the art, including, but not limited, a ball joint, ball and socket joint, hinge joint, pivot joint, prismatic joint, and the like, or any combination thereof. For example, the second joint 230 can be a ball joint.

The second joint 230 can be connected to the second mechanism 220. For example, the second joint 230 can be slidably connected to the second guide rods 226, 228 of the second mechanism 220. As illustrated in FIG. 1, with respect to the first joint 130, the second joint 230 can similarly be slidably connected to the second x-axis guide rod 226. Alternatively, or in addition, the second x-axis guide rod 226 can be slidably connected to the second y-axis guide rod 228. For example, the second x-axis actuator 222 can actuate the second joint 230 to move along the second x-axis guide rod 226 and the second y-axis actuator 224 can actuate the second x-axis guide rod 226 to move along the second y-axis guide rod 228. The second mechanism 220 can thereby move the second joint 230 with two degrees of freedom.

The second joint 230 can be configured to receive a distal portion of the surgical tool 250 and the first joint 130 can be configured to receive a proximal portion of the surgical tool 250. The first joint 130 can be configured to be a free fit with respect to the surgical tool 250. Alternatively, or in addition, the second joint 230 can be configured to be a press fit with respect to the surgical tool 250. The first joint 130 and second joint 230 can be configured to move independently, in both and x-axis and y-axis direction, providing the surgical tool with four degrees of freedom motion. Alternatively, or in addition, a user can control a fifth degree of freedom of the surgical tool, depth. For example, a clinician can control the depth of a needle in the patient.

The one or more fiducial markers can include a first fiducial marker 140 and a second fiducial marker 240. The one or more fiducial markers can be positioned to reflect the position of the surgical tool 250. For example, the first fiducial marker 140 can be connected to the first joint 130 and the second fiducial marker 240 can be connected to the second joint 230. Alternatively, or in addition, the one or more fiducial markers can be coaxial with a line between the first and second joint 130, 230. For example, the first and second fiducial markers 140, 240 can be coaxial with the surgical tool. Alternatively, or in addition, the one or more fiducial markers can be symmetrical with a line between the first and second joint 130, 230. The first and second fiducial markers 140, 240 can be located between the first planar stage 110 and the second planar stage 210. Alternatively, or in addition, the first and second fiducial markers 140, 240 can be located both above the first planar stage 110, both below the second planar stage 210, one above and one below the first planar stage 110, one above and one below the second planar stage 210, one or both in between the first and second planar stages 110, 120, or any combination thereof.

The one or more fiducial markers can include an MRI-visible substance. For example, the fiducial markers can include any substance that will show up in an MRI such as vitamin E. Alternatively, or in addition, the fiducial markers can be symmetrical in shape (e.g., a sphere, donut) such that the fiducial marker will appear as symmetrical in the imaging plane of an MRI machine. For example, the fiducial markers can include a polymer spherical shell with a hollow spherical cavity filled with Vitamin E.

Figure 24:
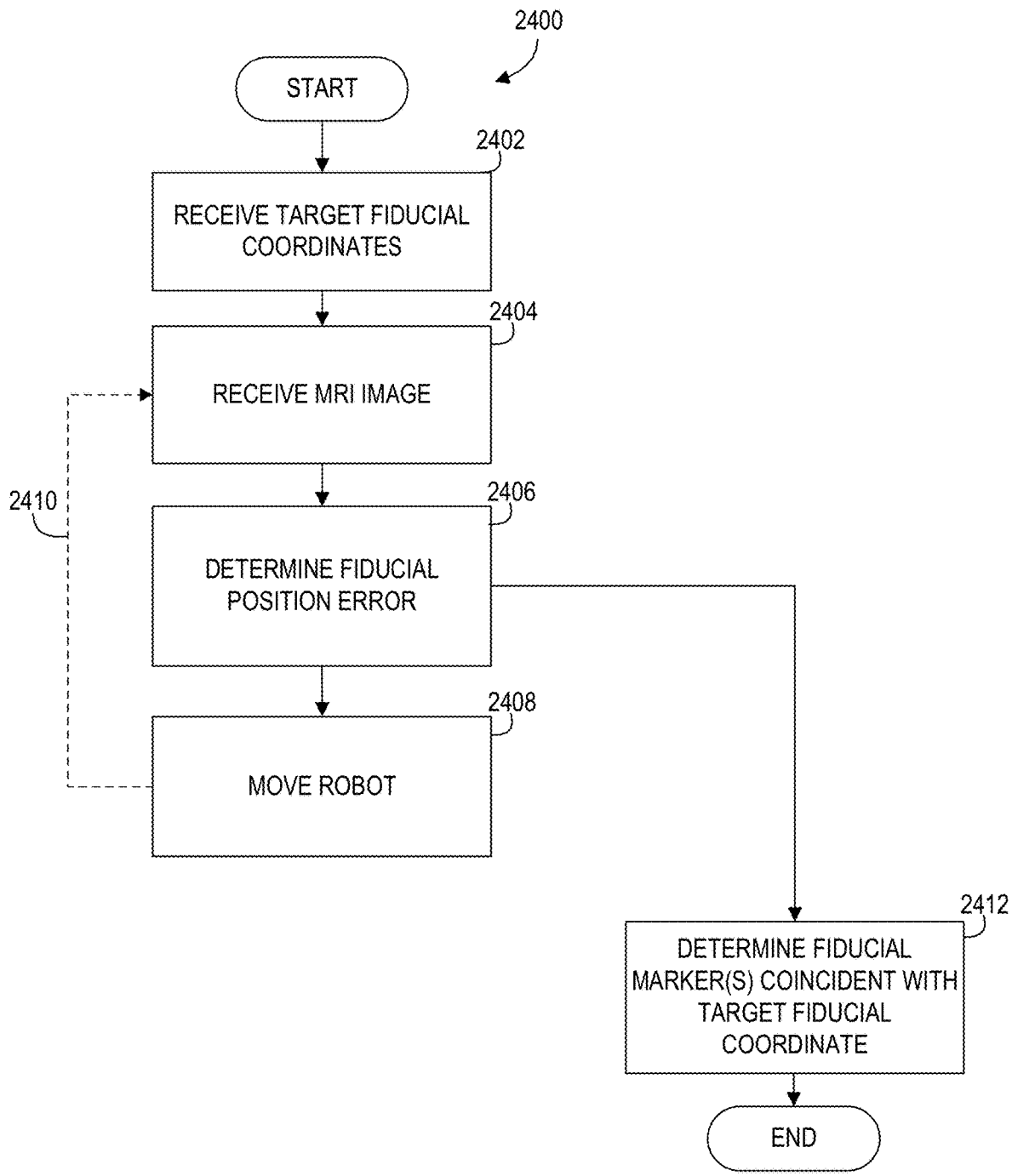
FIG. 24 provides a flow chart illustrating an example method for robotic surgery, in accordance with the present disclosure.

The disclosed technology includes methods for surgical instrument positioning, such as method 2400, which is illustrated in FIG. 24. Method 2400 and/or any other method described herein can be performed by a controller or computer. Method 2400 can be a method where a surgical tool is moved by a robot to a desired position based, at least in part, on visual servoing.

The method 2400 can include receiving 2402 target fiducial coordinates. The target fiducial coordinates can be a desired position of one or more fiducial markers of a surgical tool. For example, the target fiducial coordinates can be indicative of the desired position of a first and second fiducial marker, the first and second fiducial markers being indicative of the position of a surgical tool and wherein, when the first and second fiducial markers are in the desired position, the surgical tool will be in the desired position.

The method 2400 can include receiving 2404 an MRI image. The Mill image can include the position of the one or more fiducials. Additionally, the Mill image can include an image of the body or a portion of the body of a patient. For example, the MM image can include an image of the spine of the patient.

The method 2400 can include determining 2406 the fiducial position error. The fiducial position error can be based, at least in part, on the position of the one or more fiducial in the MRI image and the target fiducial coordinates.

The method 2400 can include moving 2408 the robot. For example, the method 2400 can include moving, by one or more actuators, the surgical tool to a new position based at least in part on the fiducial position error.

The method 2400 can include repeating 2410 some or all of steps 2404, 2406, and 2408. The repeating 2410 can be done to make the method 2400 an iterative process where the fiducial position error is driven towards zero.

The method 2400 can include determining 2412 that the one or more fiducial markers are coincident with the target fiducial coordinates. For example, the method 2400 can include after determining 2406 the fiducial position error, determining 2412 that that fiducial position error is zero or within an acceptable range to zero, indicating that the one or more fiducial markers are coincident with the target fiducial coordinates. This can indicate that the surgical tool is in the desired position and that the robot does not need to move the surgical tool again.

Figure 25:
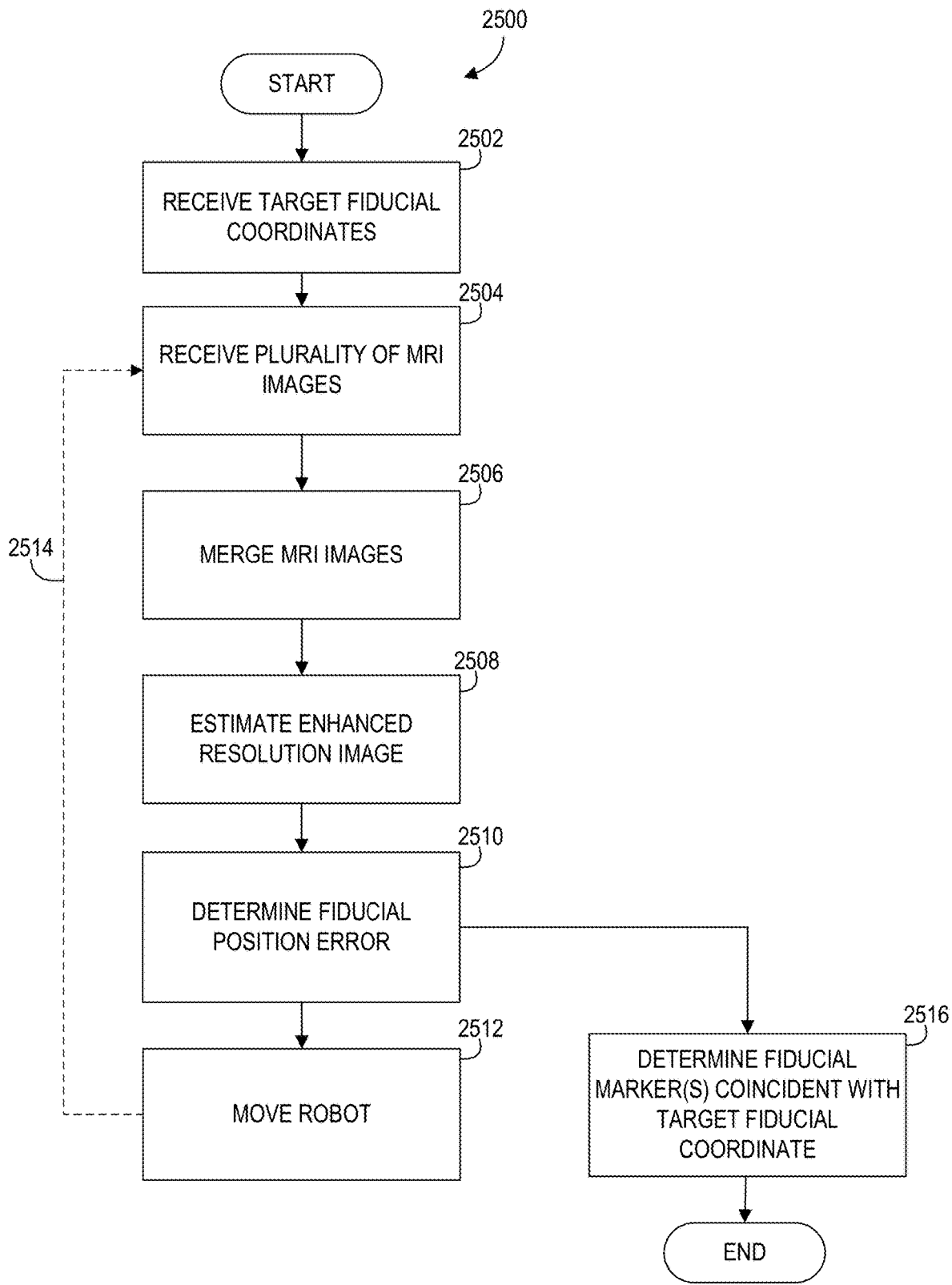
FIG. 25 provides a flow chart illustrating an example method for robotic surgery, in accordance with the present disclosure.

The disclosed technology includes method 2500 for surgical instrument positioning, which is illustrated in FIG. 25. Method 2500 and/or any other method described herein can be performed by a controller or computer. Method 2500 can be a method where a surgical tool is moved by a robot to a desired position based on MM images that have been enhanced. Method 2500 can be a method where a surgical tool is moved by a robot to a desired position based, at least in part, on visual servoing. Method 2500 can be a method where an MRI image resolution is enhanced through merging multiple Mill images. For example, the Mill image can be enhanced based, at least in part, on a super resolution method.

The method 2500 can include receiving 2502 target fiducial coordinates. The target fiducial coordinates can be a desired position of one or more fiducial markers of a surgical tool. For example, the target fiducial coordinates can be indicative of the desired position of a first and second fiducial marker, the first and second fiducial markers being indicative of the position of a surgical tool and wherein, when the first and second fiducial markers are in the desired position, the surgical tool will be in the desired position.

The method 2500 can include receiving 2504 a plurality of MM images. The Mill images can include the position of the one or more fiducials. Additionally, the Mill image can include an image of the body or a portion of the body of a patient. For example, the MRI image can include an image of the spine of the patient. The plurality of Mill images can be spatially shifted images. For example, each of (or some of) the plurality of images can be spatially shifted by a known amount. The images can be spatially shifted by displacing the fiducial markers by a known amount. For example, instead of moving the image acquisition component of the MRI, one or more actuators of the robot can displace the fiducial markers by known amounts.

The method 2500 can include merging 2506 the plurality of images. For example, the plurality of images can be collected and combined so that they can be used to estimate a resolution-enhance image based, at least in part, on the plurality of images.

The method 2500 can include estimating 2508 an enhanced-resolution image, based, at least in part, on the merged plurality of images. The enhanced-resolution image can include the position of the one or more fiducials. The estimating 2508 can include reconstructing the plurality of images to create a new image that has a higher resolution that that of the original plurality of images. For example, the estimating 2508 can include a super resolution imaging technique for processing the plurality of images to create a higher resolution image. The estimating 2508 can therefore produce an image that has a higher resolution than the highest resolution that the MM machine is capable of capturing.

The method 2500 can include determining 2510 the fiducial position error. The fiducial position error can be based, at least in part, on the position of the one or more fiducial in the MRI image and the target fiducial coordinates.

The method 2500 can include moving 2512 the robot. For example, the method 2500 can include moving, by one or more actuators, the surgical tool to a new position based at least in part on the fiducial position error.

The method 2500 can include repeating 2514 some or all of steps 2504, 2506, 2508, 2510, and 2512. The repeating 2514 can be done to make the method 2500 an iterative process where the fiducial position error is driven towards zero.

The method 2500 can include determining 2516 that the one or more fiducial markers are coincident with the target fiducial coordinates. For example, the method 2500 can include after determining 2510 the fiducial position error, determining 2516 that that fiducial position error is zero or within an acceptable range to zero, indicating that the one or more fiducial markers are coincident with the target fiducial coordinates. This can indicate that the surgical tool is in the desired position and that the robot does not need to move the surgical tool again.

The method 2500 can be performed subsequent to the method 2400. For example, the image resolution enhancement of method 2500 can be performed after determining 2412 that the fiducial markers are coincident with the target fiducial coordinates based on an original (e.g., not resolution enhanced) Mill image.

The following examples further illustrate aspects of the present disclosure. However, they are in no way a limitation of the teachings or disclosure of the present disclosure as set forth herein.

EXAMPLES

Recent developments in the field of cellular therapeutics have indicated the potential of stem cell injections directly to the spinal cord. This injection procedure allows for direct delivery of cellular therapeutics, avoiding the need for diffusion. The targeted area is very small, with a narrow trajectory necessary to avoid vertebrae and other sensitive tissues. To improve both the speed and accuracy of a minimally invasive MRI based procedure, an MM compatible robotic needle positioning system is developed in this disclosure. The robot uses linear piezoelectric motors to directly drive a parallel plane positioning mechanism. Feedback is provided through Mill images taken during the orientation procedure. This system is found to be capable of orienting a needle endpoint to within 14 microns of a desired position. The robot is also found to be fully Mill compatible. The high accuracy of this needle positioning robot and visual feedback method will result in a significant improvement to the workflow of spinal injection procedures.

Methods and Results

A. Mechanical Design

Specifications: The primary target for cellular therapeutics in the spinal cord is the ventral horn. Although the spinal cord as a whole is around 12 mm in diameter, the ventral horn is much smaller, with a cross sectional area near 1 $mm^2$. For this reason, accuracy of the entire robot and visual feedback system must be better than 1 mm. In order to ensure placement with high fidelity inside the ventral horn, this work targeted robot accuracy at 100 microns. The 6 minute MPRAGE MRI sequence used provides pixel resolution of 1 mm. Thus for the entire MRI based system, desired accuracy was set at 1 mm. Time is a critical component of this system, as the primary motivation is to improve timing and accuracy of cellular therapeutic injection. The robot and feedback system should require 2 positioning updates to reach a desired trajectory, in order to minimize scanner time.

Figure 4A:
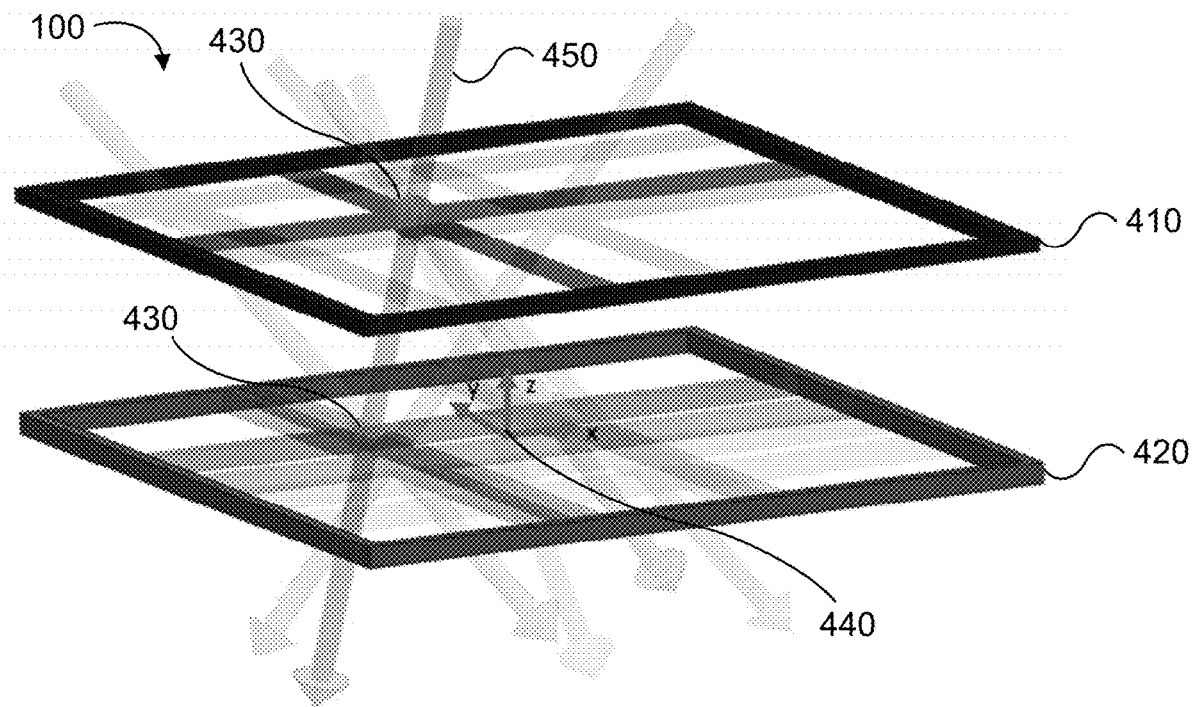
FIG. 4A provides a diagram of positioning concepts, in accordance with the present disclosure.

Parallel Plane Positioning Mechanism: To avoid remote actuation and the necessity of rotary actuators for controlling rotational degrees of freedom (DOF), a parallel plane mechanism was chosen. The parallel plane positioning concept is shown in FIG. 4A. FIG. 4A provides a needle 450 positioning concept of a robot 100 with an upper stage 410, a lower stage 420, ball joints 430 and the origin 440, which is at the center of the lower stage 420. Both the upper and lower ball joints 430 can move independently, controlling 4 DOF of the needle guide.

The mechanism consists of 2 parallel planar stages each manipulating a ball joint. The cannula runs through these ball joints, by actuating the 4 planar axes, 4 actuated DOF are achieved, the fifth DOF, needle depth, is controlled by the surgeon inserting the needle into the cannula. The sixth DOF, needle rotation, is irrelevant for this procedure. Because the actual distance between the ball joints is dependent on the orientation, the cannula is fixed in lower joint, while the upper joint allows the cannula to slide through the center of the ball joint.

The following equations can be used to relate the needle position to the Cartesian coordinates of the two ball joints. Needle orientation, o, is determined by the relative position of the upper and lower joints, $$o = \|U-L\| \quad \text{Equation 1:}$$

Where U and L are the upper and lower ball joint positions, respectively. The target position at an injection depth of l from the lower ball joint is then l in the direction of negative o.

$$T = -l\|U-L\| \quad \text{Equation 2:}$$

One of the important aspects of the needle positioning task are the rotations about the X and Y axes, as shown in FIG. 4A. These angles are determined by the relative Y and X coordinates respectively. The angles are given as, $$\theta_x = a \tan 2(h, y_r),$$

$$\theta_y = a \tan 2(h, x_r),$$

$$\theta_z = a \tan 2(y_r, x_r) \quad \text{Equation 3:}$$

Where h is the distance between the planes, and $x_r = x_{upper} - x_{lower}$ and $y_r = y_{upper} - y_{lower}$ are the relative x and y positions of the ball joints.

Figure 5:
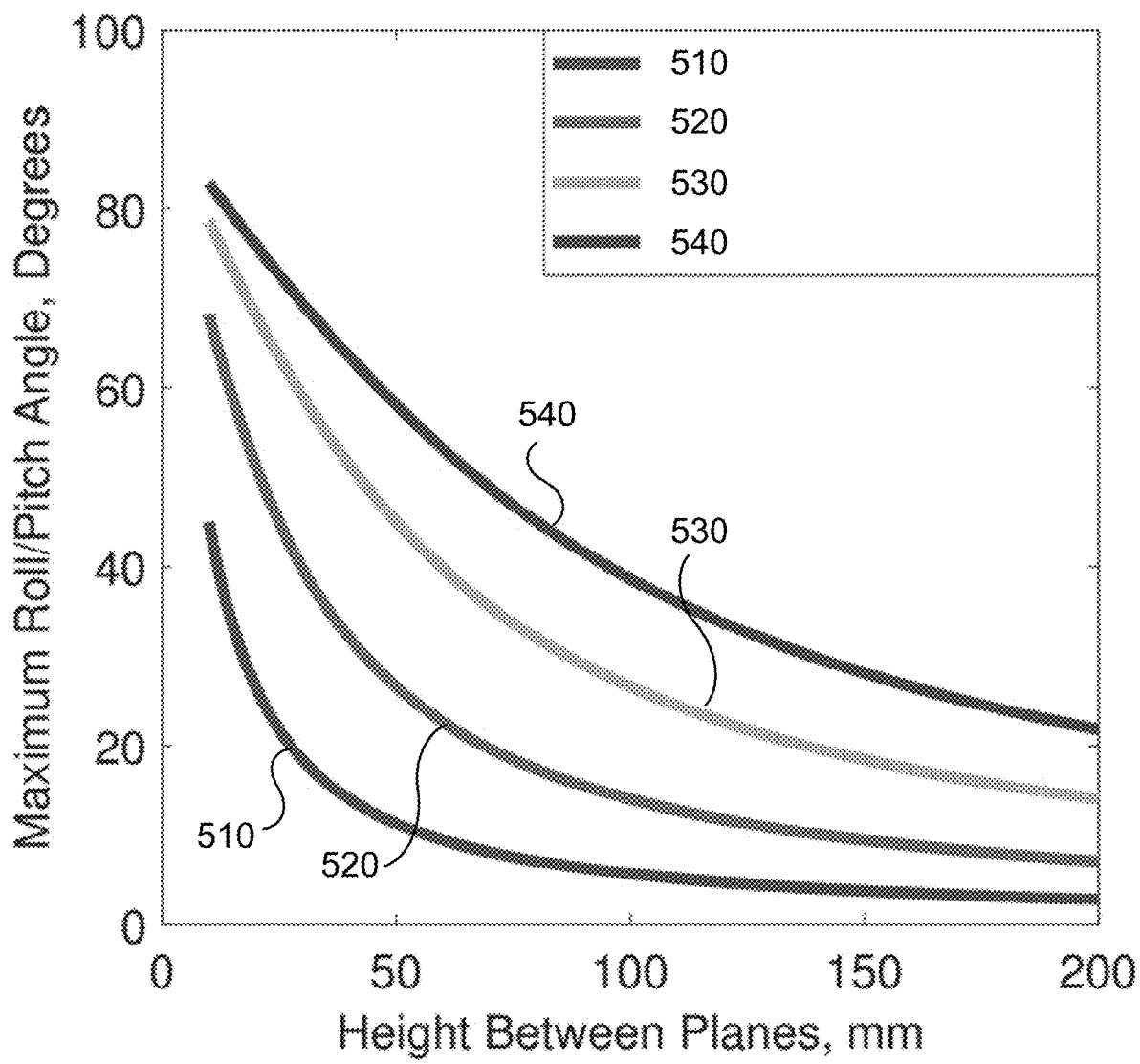
FIG. 5 provides a graph of positioning ranges, in accordance with the present disclosure.

From Equation 3, it is clear that the angular range of the robot will be determined by the travel of the upper and lower stages, as well as the distance between the two. This is reflected in FIG. 5. FIG. 5 provides positioning ranges for varied actuator travel (10 mm actuator range 510, 25 mm actuator range 520, 50 mm actuator range 530, and 80 mm actuator range 540) and plane distances. Physical limitations constrain the minimum value for h, the height between the planes, while larger values reduce the angular positioning capability.

Figure 6:
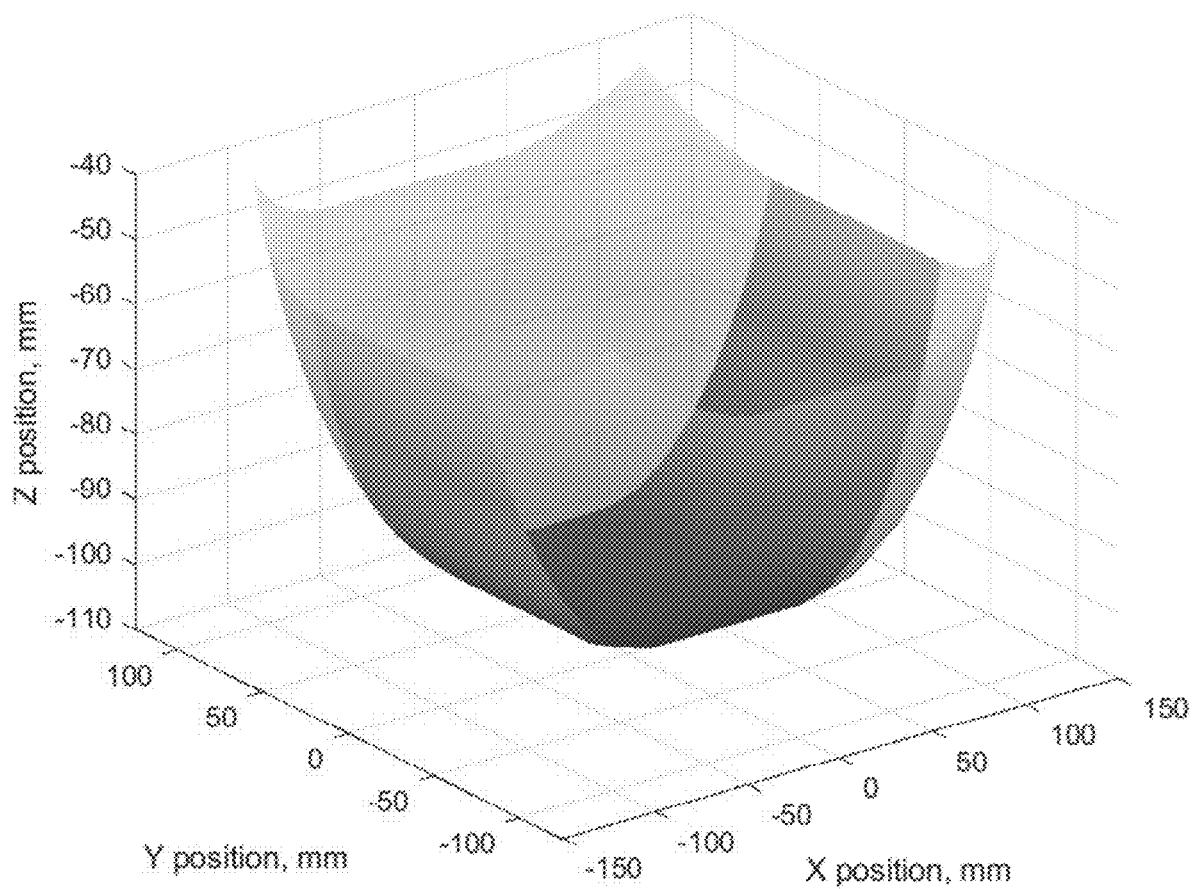
FIG. 6 provides a graph of the workspace of a surgical robot, in accordance with the present disclosure.

Workspace Analysis: The workspace of the parallel plane needle positioning robot is shown in FIG. 6. The transparent surface is the reachable surface with any set of angles, while the solid surface is the reachable surface when the angle about the X axis, Ox, is restricted to less than 15 degrees. Due to the height of the robot above the patient, and observed geometry of the lumbar vertebrae, this is a reasonable restriction.

Actuators: Positioning accuracy of the needle guide is the critical aspect of this robot. For this reason, direct drive linear motors were chosen to reduce backdrivability and backlash. Linear piezoelectric motors were chosen because of their MM compatibility and high precision.

These linear motors are uniquely suited for the desired high resolution positioning, as they have a step size of 4-7 microns, consume no power when maintaining a fixed position, and are MRI compatible. The ability to place these actuators inside the bore of the scanner allows a rigid link between drive rods and the robot frame, eliminating the need for gearing or a cable drive, and the associated backlash and deformation problems.

Design: The parallel plane robot design prioritized MRI compatibility and structural rigidity to ensure accuracy and avoidance of contamination of the MRI images needed to targeting of the spinal cord. 4 DOF positioning is accomplished through the use of 2 sets of perpendicular actors, with the X axis assembly mounted to the Y axis actuator. The robot consists of two nearly identical stages, with a single one shown in FIG. 1. The needle guide passes through both the upper and lower ball joints, and these joints translate in the plane to provide 4 DOF positioning.

The Y axis actuator moves the entire X axis assembly along the outer guide rods, while the X axis actuator is mounted to this assembly, and moves only the center ball joint, collar and fiducial. Each actuator is centered between the guide rods, to avoid unbalanced loads on the drive rods. Guide rods are low friction acetal resin, and sleeve bearings are press fit into the X assembly components and collar to decrease friction.

The only difference between the upper and lower stages is in the diameter of the needle guide hole in their respective ball joints. The lower stage has a press fit, while the upper stage is a free fit, to allow the guide to slide freely. The lower base also has additional features for mounting above the spinal cord phantom used in this study. The full robot CAD model is shown in FIG. 2. Four rigid brackets 260 connect the upper and lower stages, these brackets also provide the mounting points for the lower stage Y Axis guide rods.

Figure 3A:
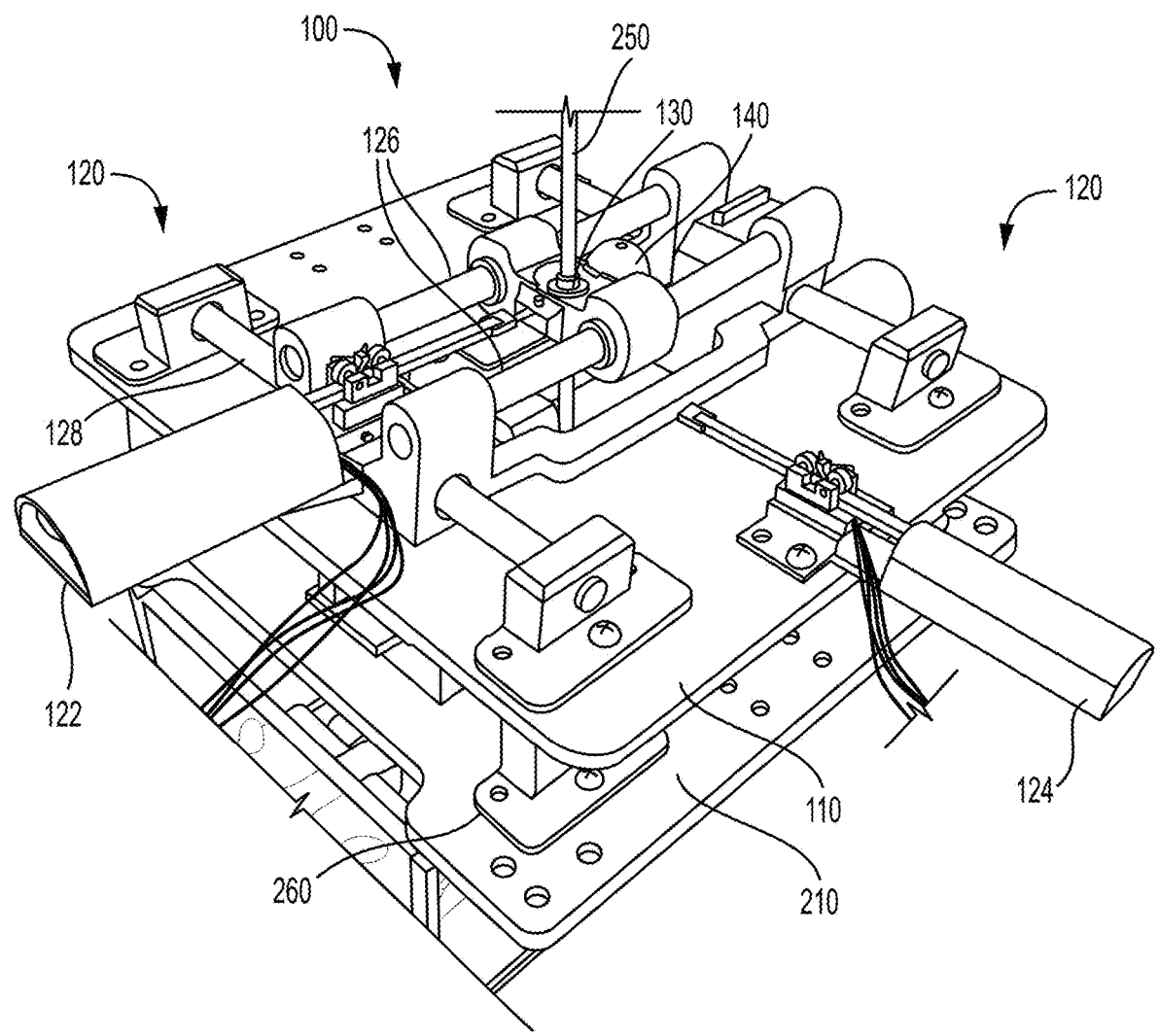
FIG. 3A provides photo of a surgical robot, in accordance with the present disclosure.

Materials and Fabrication: The robot described in the preceding section was fabricated from a variety of MRI compatible materials using both conventional machining and FDM printing. FDM parts were printed in ABS plastic, while machined parts consisted of Acetal resin. The needle guide was cut from 4 mm brass tubing. Fasteners were titanium and nylon. The completed robot is shown in FIG. 3A.

B. Visual Servoing Control

The magnetic resonance imaging modality enables simultaneous visualization of both internal anatomical structures as well as contrasting landmarks (fiducials) placed on the robot. For a clinical application such as needle insertion, the surgeon delineates a desired final pose of the tool with respect to the patient's anatomy. This step is often performed via a graphical software interface, e.g., as a vector line drawn between adjacent vertebrae in a 3D-reconstructed MRI image. The locations of the robot fiducials corresponding to the needle being co-axial with this desired vector pose defines their desired target locations. Visual servoing control uses image information to actuate the robot's axes in order to drive the fiducial position errors to zero. The method does not require sensor calibration and assumes no a priori knowledge of robot kinematics.

Figure 7A:
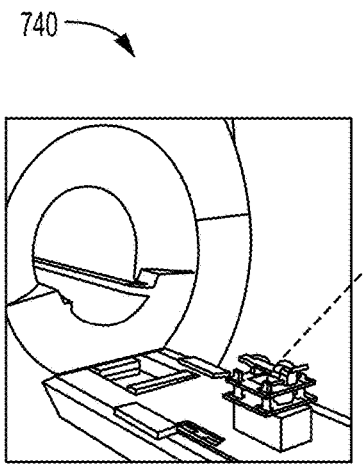
FIG. 7A provides a photo of an MRI evaluation setup, in accordance with the present disclosure, in accordance with the present disclosure.
Figure 7B:
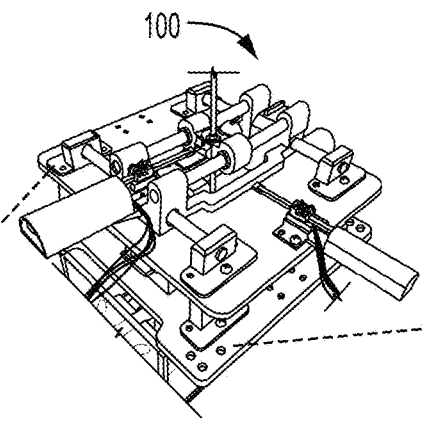
FIG. 7B provides a photo of a surgical robot, in accordance with the present disclosure, in accordance with the present disclosure.
Figure 7C:
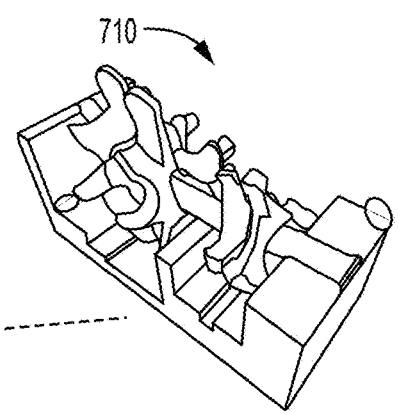
FIG. 7C provides a photo of a spinal cord phantom, in accordance with the present disclosure, in accordance with the present disclosure.
Figure 7D:
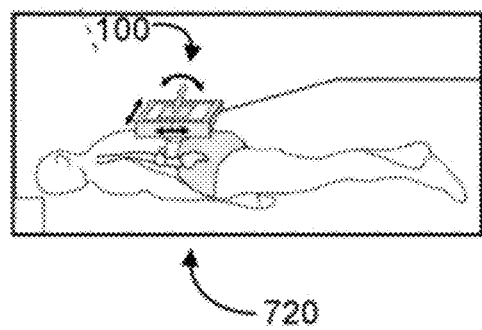
FIG. 7D provides a diagram of an MRI-compatible surgical robot, in accordance with the present disclosure.
Figure 7E:
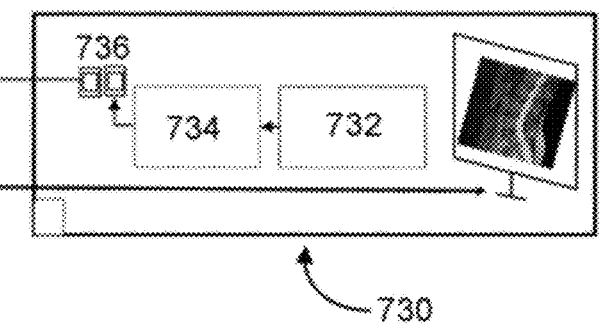
FIG. 7E provides a diagram of a surgical robot control method, in accordance with the present disclosure.

In this disclosure, the visually tracked fiducials are rigidly affixed to the robot stages. Planar slices of the 3D MPRAGE scan (see FIG. 9) are evaluated for the 2D pixel coordinates of the center of each of the upper and lower stage fiducials. The visual feedback schematic and detail view of the robot is shown in FIG. 7. FIG. 7 provides an MRI visual feedback schematic with FIG. 7A showing 3T MM 740 and robot 100, FIG. 7B showing a closeup of the robot 100, FIG. 7C showing a spinal phantom 710, FIG. 7D showing a scanner diagram 720, and FIG. 7E showing a control room diagram 730 including image processing 732, motion controller 734, piezo driver 736, and electrical wire 738.

The desired fiducial coordinates were obtained by manually actuating the robot axes to effect a proper needle pose with respect to the spinal cord phantom and then designating the resulting coordinates the desired ones. The image-based visual servoing control implemented is listed as Algorithm 1.

---
Algorithm 1: Imaged-Based Visual Servoing Control
---
known: desired fiducial pixel coordinates.
   desiredFidCoords;
initialize: jog each robot axis and note corresponding
   change in image pixel coordinates to obtain numerical
   approximation of image jacobian matrix, J;
   normPixelError = large value;
while normPixelError > 1 do
| Take MRI Image;
| pixelErrorVector = actualFidCoords −
|   desiredFidCoords;
| normPixelError = ||pixelErrorVector||;
| Update Actuators by $-J^{-1}$ pixelErrorVector;
end

---

C. MRI Compatibility

Figure 8:
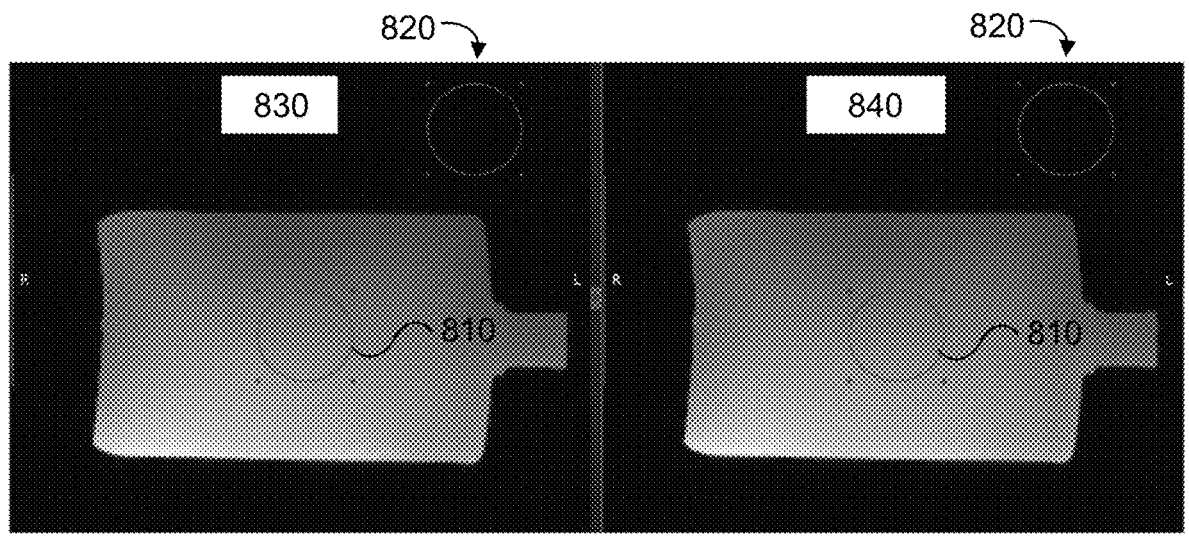
FIG. 8 provides images of an experimental cylindrical phantom with and without a robot, in accordance with the present disclosure.

The MM compatibility of the robot was assessed in a 3 Tesla MM. Mill compatibility was measured as the Signal-to-Noise Ratio (SNR) reduction in a Nickel Sulfate solution cylindrical phantom. FIG. 8 provides images of the cylindrical phantom with the robot 830 and without the robot (control) 840, regions used in the calculation of SNR are shown, with the signal intensity taken from the circles 810 and noise taken from circles 820. Three dimensional scans were performed under 2 different operating conditions, the first with only the phantom and RF coil in the scanner, and the second with the robot placed above the phantom. The imaging sequence used was the MPRAGE sequence, and scan parameters were identical throughout.

SNR was measured as the mean intensity in a 16 cm2 circular region in the center of the phantom divided by the standard deviation of an identical region in air. The calculated SNRs were 244.06 for the control image with no robot, and 230.226 for the robot. This gives a SNR reduction of 5.7% for the robot, well within the 10% reduction criteria for MRI compatibility. It is likely that shielding of the actuator cables would additionally mitigate the SNR reduction observed. The SNR was not measured during actual movement of the robot, as the information from each successive image is necessary to update the robot position, and thus the positioning protocol does not require simultaneous actuation and imaging.

D. Phantom Construction

A phantom spinal cord and vertebrae were constructed for evaluation of the robot. CAD models from the BodyParts3D database were used to create a model spinal cord and section of vertebrae. L3-L4 and C3-C4 were the chosen vertebrae, to give a range of anatomical constraints for injection sites. The vertebrae and mounting fixture were manufactured in ABS plastic with a FDM printer. The same printer was used to create a 2 part mold for casting the spinal cord phantom. The cord was cast from a 2 part silicone that is MR-visible. This phantom 710 is shown in FIG. 7C. The phantom was used to set target needle trajectories that avoid the vertebrae.

E. Repeatability and Accuracy Verification

Figure 11:
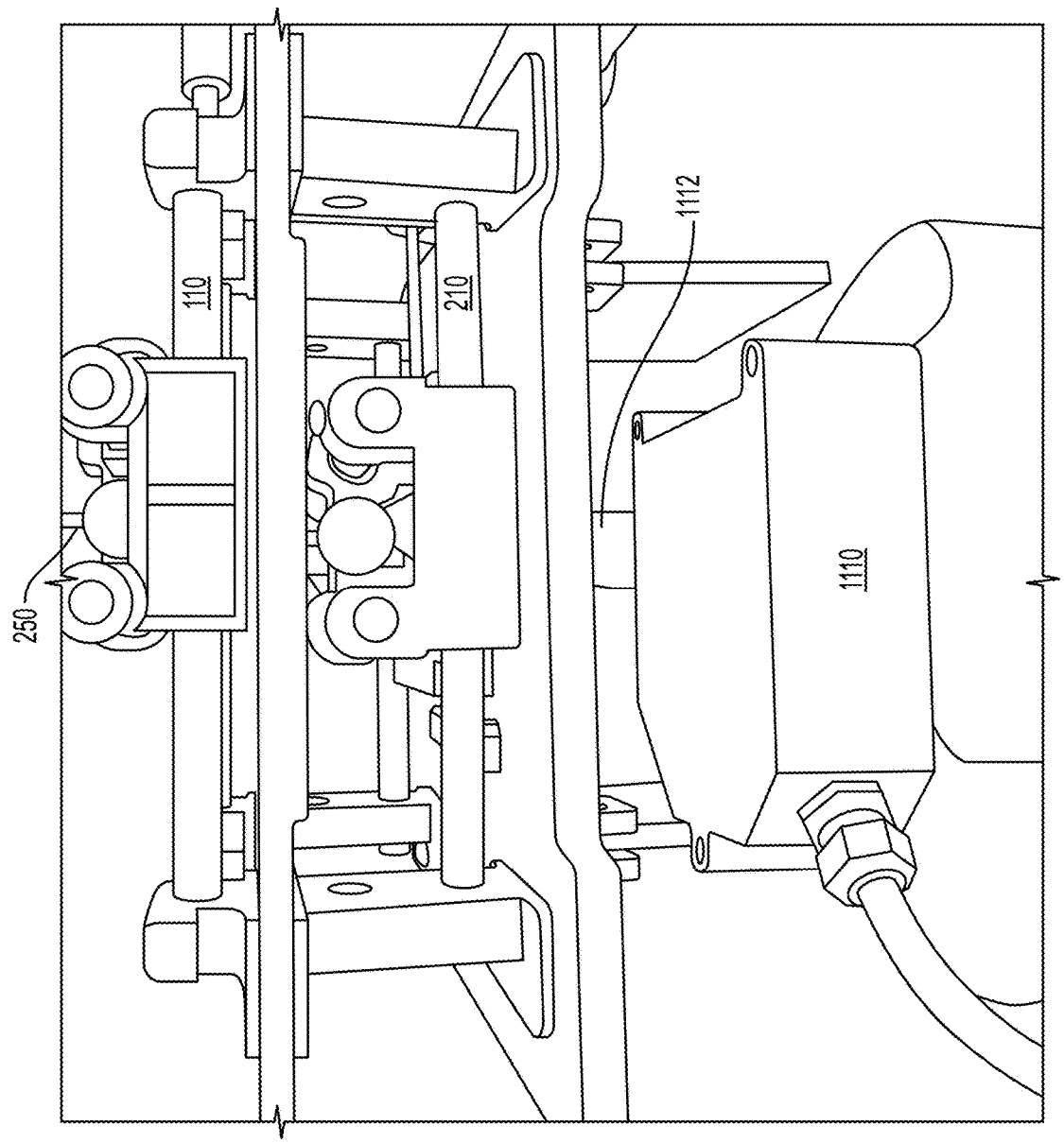
FIG. 11 provides a photo of an experimental setup, in accordance with the present disclosure.

Single axis repeatability and accuracy: The repeatability of the robot was measured with a laser triangulation sensor. The experimental setup is shown in FIG. 11 including the a laser position sensor 1110 and laser target 1112. Position was measured at the beginning of the experiment, with 10 repeated commands sent to the top X axis actuator to measure the repeatably of this motion. Subsequently, the position measurements were used iterative to move the needle guide back to the original position. The standard deviation of 10 "out and back" commands was 166.13 microns, while the error after 4 adjustments was 14 microns.

4 Axis repeatability: The above experiment was repeated, however in the second case, all 4 actuators were stepped forwards and back 10 times. The standard deviation of these motions was 192.8 microns. This shows that the open loop accuracy of the robot is well under the 1 mm resolution of the MRI scanner.

Figure 12:
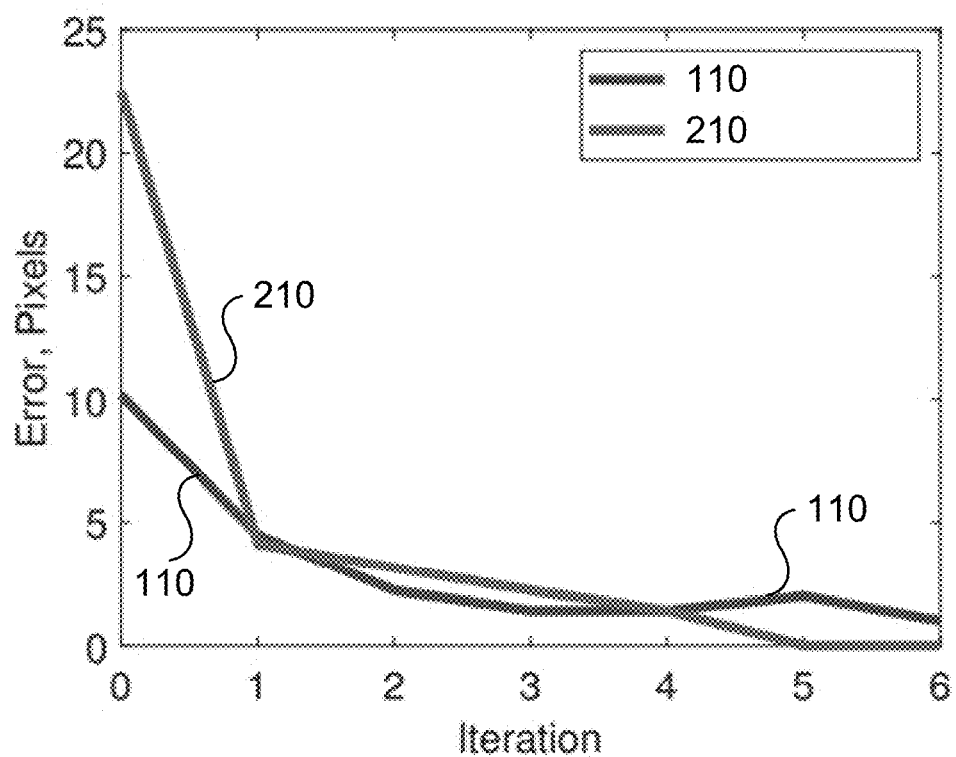
FIG. 12 provides a graph of experimentally measured positioning results, in accordance with the present disclosure.

Camera based positioning: The results presented above clearly demonstrated that the robot is capable of positioning accuracy far beyond the capabilities of the MRI scanner. In order to better capture the positioning capabilities of the robot, camera based visual servoing was applied. A camera placed above the upper stage of the robot captured the planar position of both upper and lower stage fiducials. The resolution of the camera was 30 microns for the top fiducial, and 104 microns for the bottom, with this disparity occurring due to the different distances from the camera lens. The visual servoing method presented in this disclosure was then applied, with results shown in FIG. 12. FIG. 12 provides the camera positioning results for the upper and lower stages 110, 210. After 6 iterations, the top stage was within a single pixel of the target location, while the bottom stage reached the target location within 5 iterations. The absolute maximum errors associated with these final positions are 54 and 73 microns respectively. This error is a significant improvement upon the previously developed spinal injection robot. Because the upper and lower stages are not coupled, once the lower stage reached its target position, further commands are not sent, without a concern that the upper stage may perturb the lower one.

Figure 9:
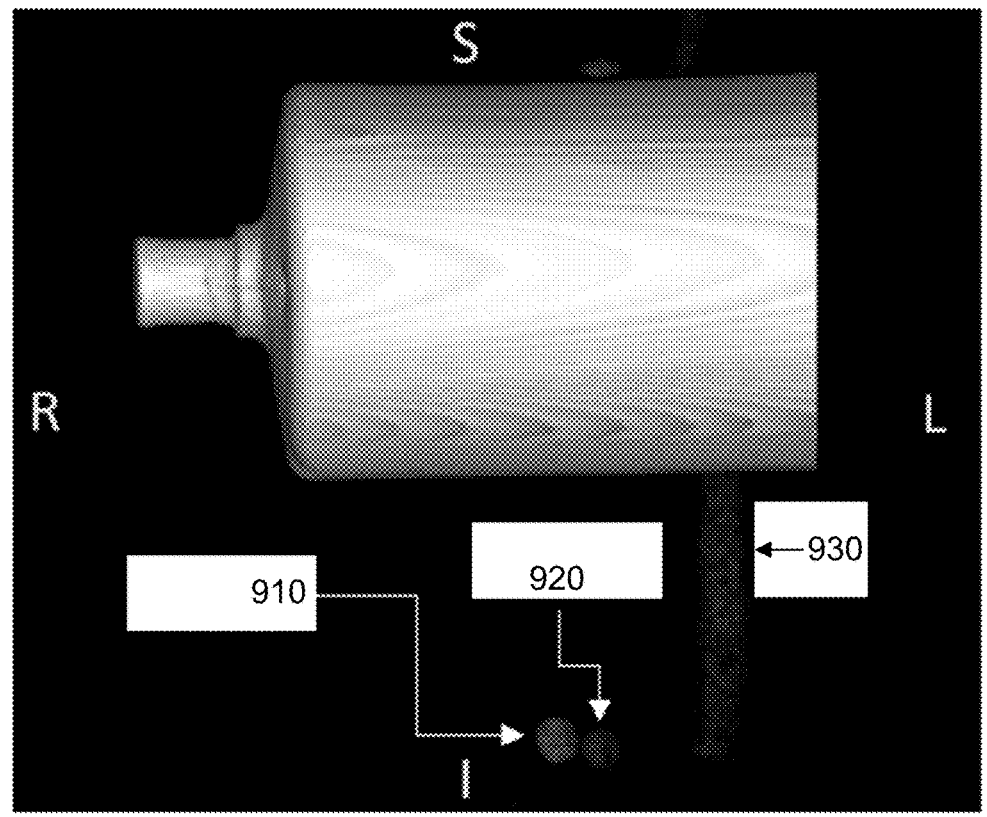
FIG. 9 provides images of an experimental cylindrical phantom and fiducials, in accordance with the present disclosure.
Figure 10:
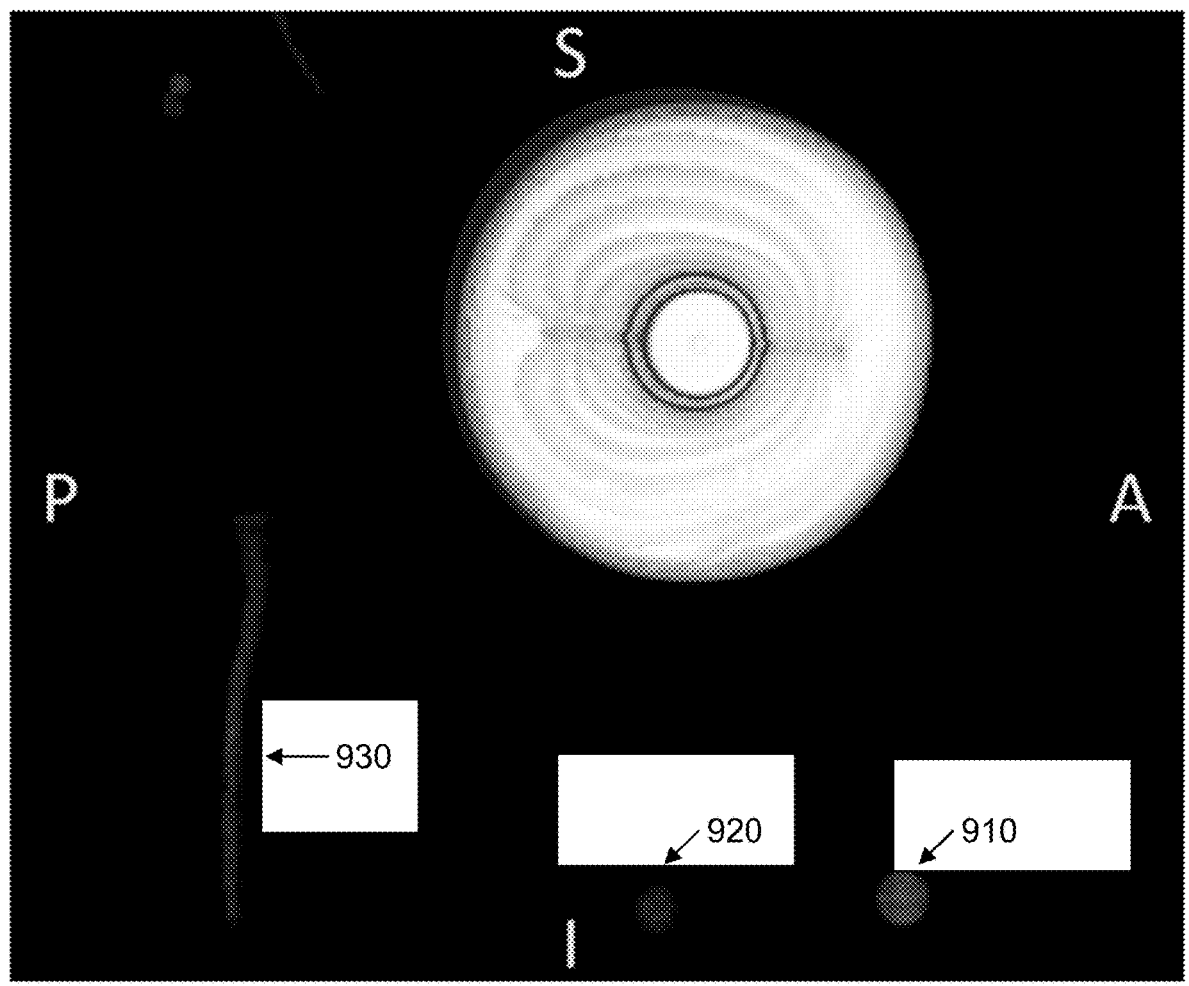
FIG. 10 provides images of an experimental cylindrical phantom and fiducials, in accordance with the present disclosure.
Figure 13:
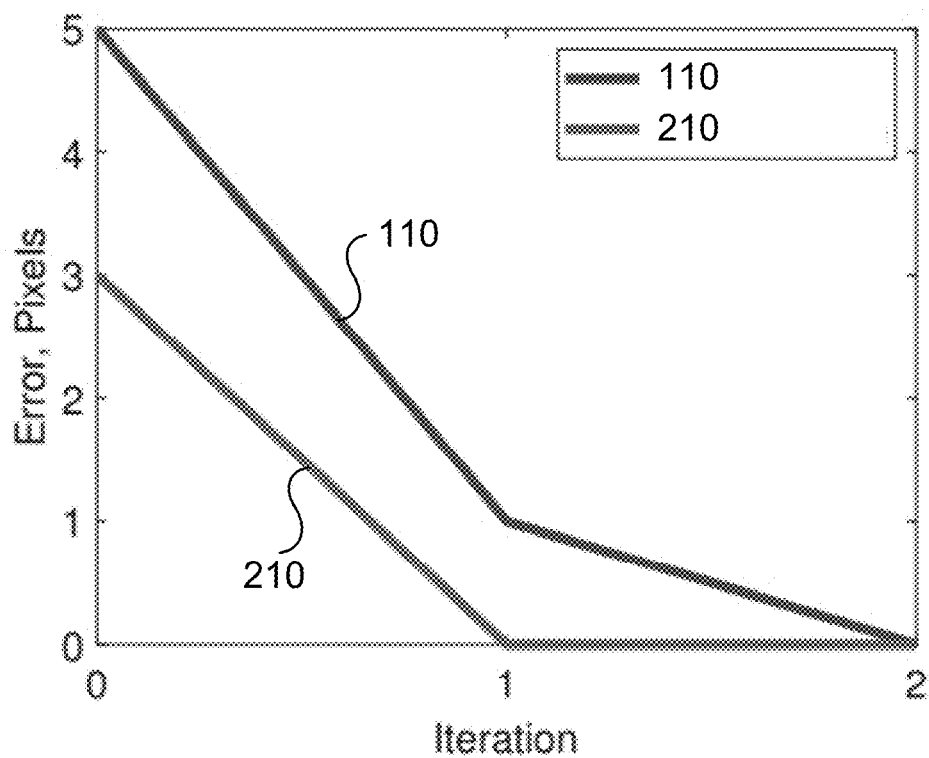
FIG. 13 provides a graph of experimentally measured positioning results, in accordance with the present disclosure.

MRI Positioning Feedback Experiments: The final experiment performed was a validation of the entire system in a 3 Tesla Mill. The same visual servoing method was applied as in the above experiments. The target position was set manually, and chosen so that a stainless steel rod inserted in the guide tube would pass between the vertebrae and into the phantom spinal cord. A total of six images were taken, with an initial image to get the target positions, 2 to compute image jacobians, and 2 more to move both stages back to the target position. Representative images are shown in FIG. 9 and FIG. 10. FIG. 9 provides an Mill view of stage fiducials and silicone spinal cord phantom including upper stage fiducial 910, lower stage fiducial 920, and spinal cord 930. R/L indicates patient right/left and S/I indicates superior/inferior. The vantage point shown is the one used for image-based visual servoing control. FIG. 10 provides an additional MM view of stage fiducials and silicone spinal cord phantom. A/P here indicates anterior/posterior. This vantage point shows an alternate view of the stages' relative locations with respect to the spinal cord. MRI positioning results from the last 3 images are shown in FIG. 13, with both the upper and lower stages reaching the target pixel after 2 updates. Targeting was confirmed by inserting the rod into the needle guide, and verifying that there was no contact with the phantom vertebrae. In this case, the absolute maximum error is 0.7 mm, or half the diagonal of a 1 mm pixel.

Discussion

A. Accuracy of the Robot

The robot accuracy was measured in three different experiments with three different measurement methods. The MM positioning experiments demonstrate that the system works as expected in the Mill environment. Only 2 position updates are required to reach a target pixel with both the upper and lower stages.

Camera based positioning experiments showed that if the imaging feedback is provided at a higher resolution, the robot is capable of higher accuracy than the MRI, with 6 updates producing positioning with a maximum error of only 54 microns in the upper stage. While the maximum error for the lower stage is slightly larger, it is likely that this is only caused 6 by the larger pixel size at that plane, as the stages are nearly identical in design and construction.

The most accurate measurements of the robots accuracy were performed with the laser triangulation sensor. In this case, the needle guide position was measured directly, instead of the upper and lower stages. This measurement then takes into account possible errors in positioning due to relative displacement of the needle guide and fiducials during movement. The repeatability tests showed that even with open loop operation of the actuators, the positioning repeatability is quite good, with a standard deviation under 200 microns, about ⅕ of the pixel size produced by the MRI.

More importantly, with the addition of simple servoing based on the position sensor, the needle could be moved to within 14 microns of the target position. This accuracy represents nearly an order of magnitude improvement upon the only previously developed MRI assisted spinal cord injection robot.

B. Visual Servoing Based on Needle Pose

Figure 14:
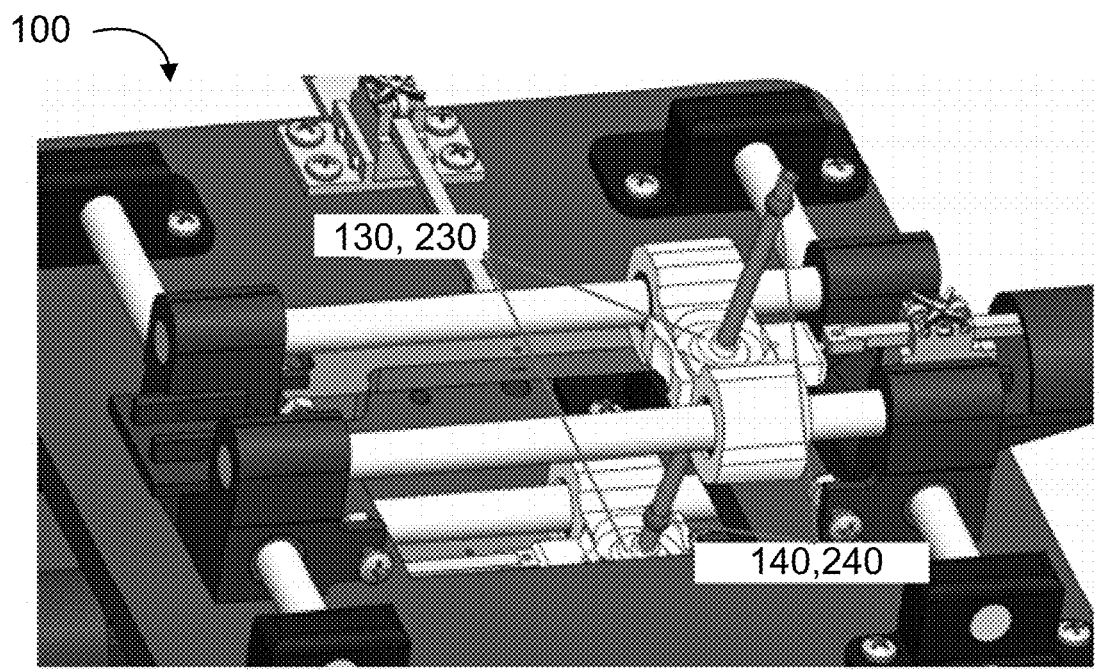
FIG. 14 provides a surgical robot, in accordance with the present disclosure.

The visual servoing-based positioning accuracy results presented in this disclosure were based on fiducials affixed to each of the two robot stages, with their desired coordinates being obtained manually. Alternatively, or in addition the fiducials could be co-axial with the needle, as shown in FIG. 14. Their desired coordinates will be computed based on a vector line drawn by a skilled practitioner (e.g., a surgeon) on the 3D MRI reconstruction. These changes will generalize the utility of the described system, remove the need for a priori information that may be difficult to ascertain in practice, and more closely align with clinical protocol.

This disclosure presents a method of navigating a surgical robot beyond the resolution of magnetic resonance imaging (MRI) by using a resolution enhancement technique enabled by high-precision piezoelectric actuation. The surgical robot was specifically designed for injecting stem cells into the spinal cord. This particular therapy can be performed in a shorter time by using an MRI-compatible robotic platform than by using a manual needle positioning platform. Imaging resolution of fiducial markers attached to the needle guide tubing was enhanced by reconstructing a high-resolution image from multiple images with sub-pixel movements of the robot. The parallel-plane direct-drive needle positioning mechanism positioned the needle guide with a high spatial precision that is two orders of magnitude higher than typical Mill resolution up to 1 mm. Reconstructed resolution enhanced images were used to navigate the robot precisely that would not have been possible by using standard MRI. Experiments were conducted to verify the effectiveness of the proposed enhanced-resolution image-guided intervention.

Autospine

A. Design

Figure 3B:
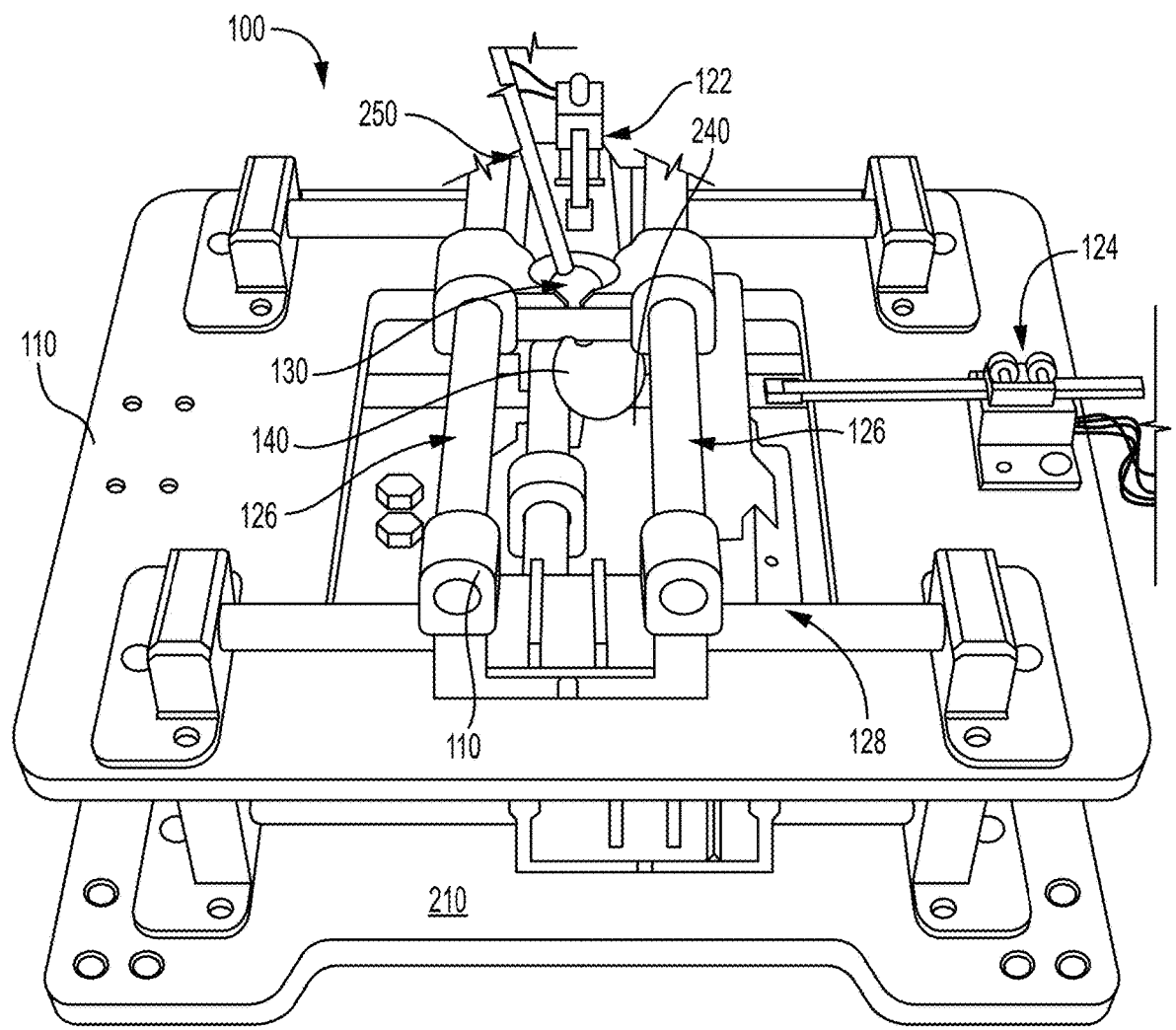
FIG. 3B provides a photo of surgical robot, in accordance with the present disclosure.
Figure 4B:
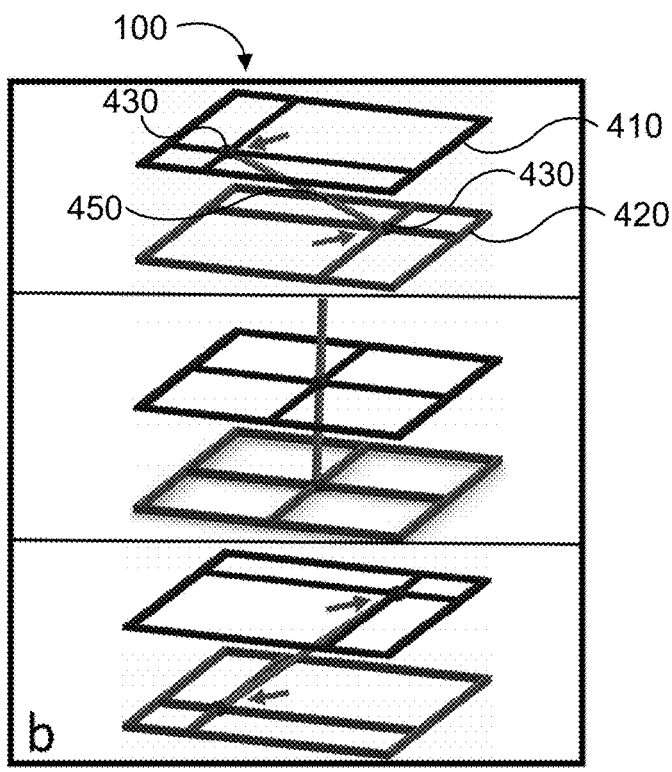
FIG. 4B provides a diagram of positioning concepts, in accordance with the present disclosure.
Figure 15:
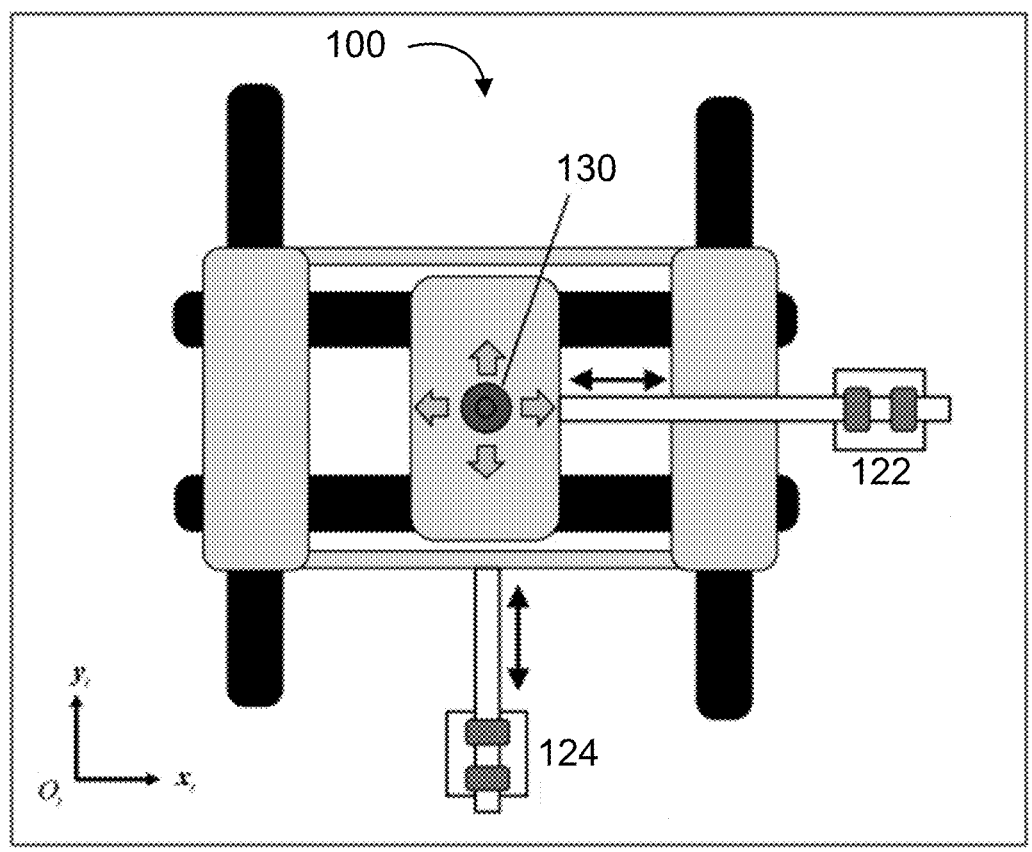
FIG. 15 provides a surgical robot, in accordance with the present disclosure.

In this disclosure, a direct-drive parallel plane mechanism ($D^2P^2$) was adopted as shown in FIG. 3B and FIG. 4B. FIG. 3B provides the AutoSPINe robot. FIG. 4B provides a parallel-plane needle guide positioning concept. Each plane is a planar x-y positioning mechanism, positioning a ball joint at the center of the stage, driven by orthogonally located linear actuators as shown in FIG. 15. FIG. 15 provides an X-Y linear stage driven by piezoelectric actuators. The upper and lower ball joints can move independently, controlling 4 DOF of the needle guide. The fifth DOF, i.e., needle depth, is controlled by the surgeon inserting the needle into the cannula. The sixth DOF, i.e., needle rotation, is irrelevant for this procedure. Because the actual distance between the ball joints is dependent on the orientation, the cannula is fixed in the lower joint, while the upper joint allows the cannula to slide through the center of the ball joint.

Figures 16A, 16B:
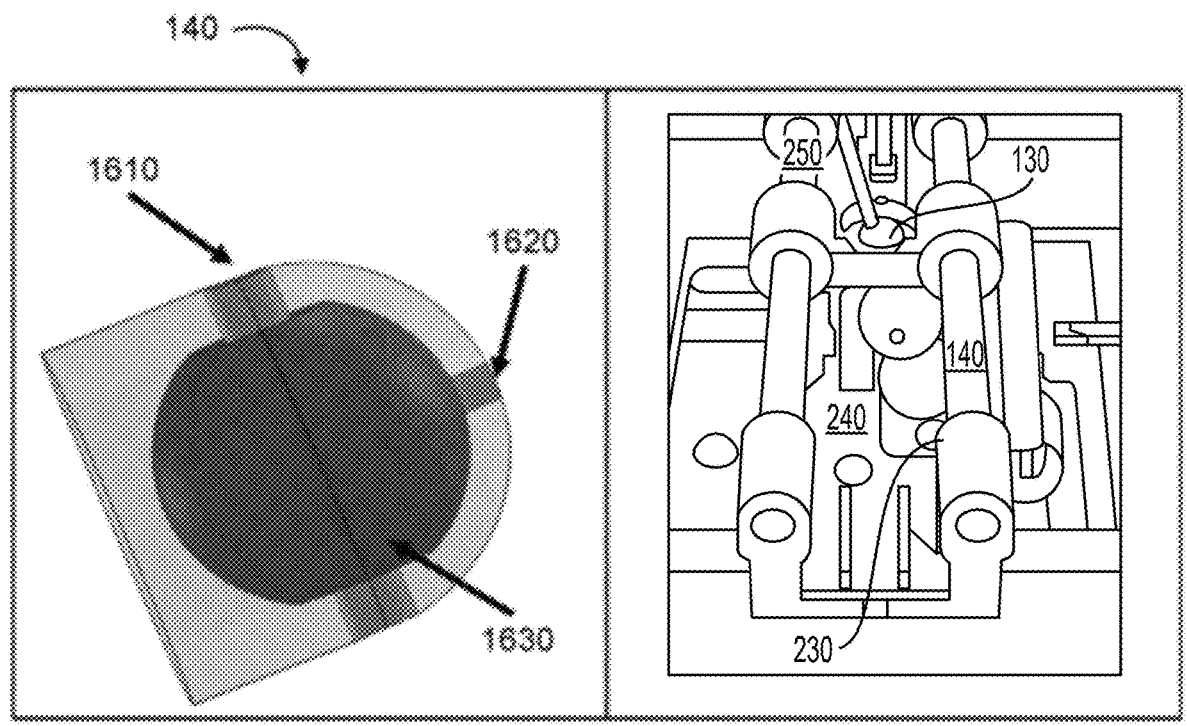
FIG. 16A provides a fiducial marker, in accordance with the present disclosure.
FIG. 16B provides a photo of a surgical robot, in accordance with the present disclosure.

The cannula and fiducial markers are of particular importance to accurate positioning of the robot, as any inaccuracies in the fiducial centers will be propagated through to the endpoint position of the needle. The cannula is composed of a 4 mm brass tube with 0.5 mm walls. Fiducials can be attached anywhere on the needle guide or X-Y stages as long as the two marker positions reflect displacements of the linear actuators. The fiducials are composed of a spherical cavity filled with Vitamin E, surrounded by a polymer shell. The CAD model of a fiducial 140 is shown in FIG. 16A including a cannula channel 1610, a filling channel 1620, and Vitamin E 1630. Upper and lower fiducials (e.g., first and second fiducial markers 140, 240) are identical. The fiducial shells were printed with polylactic acid (PLA) on a 3D printer.

B. Kinematics

Figure 17A:
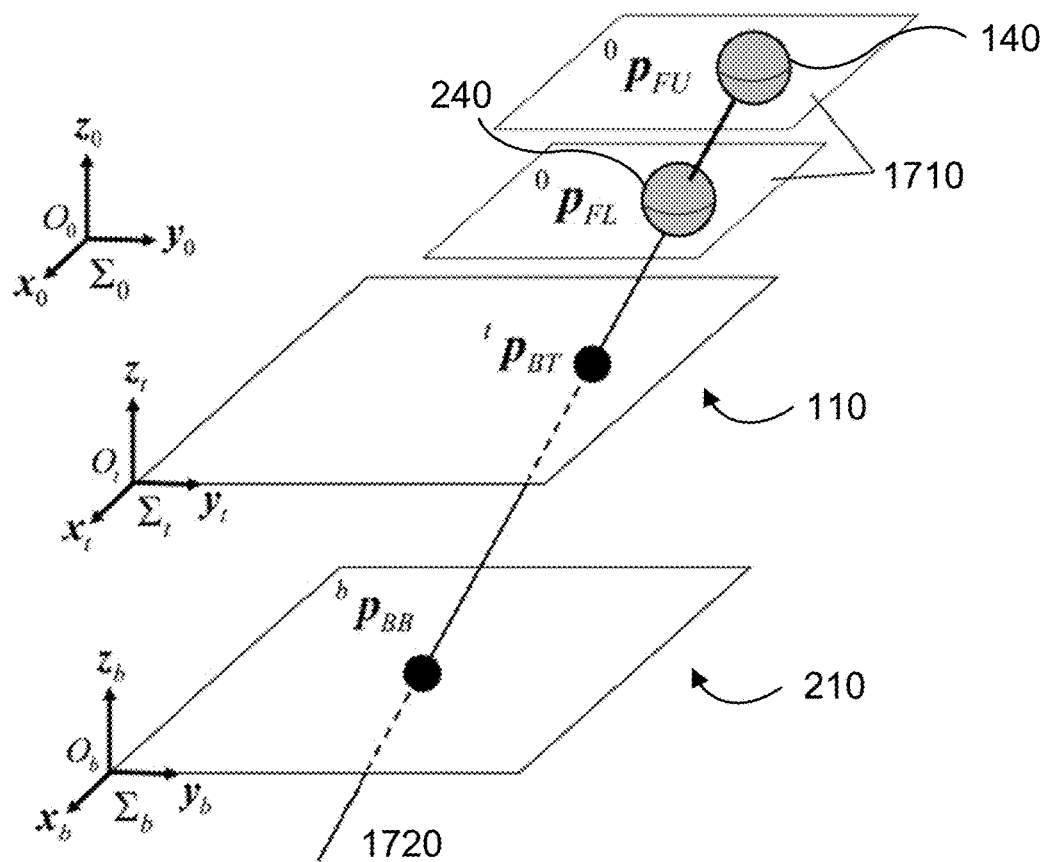
FIG. 17A provides a diagram of kinematics, in accordance with the present disclosure.
Figure 17B:
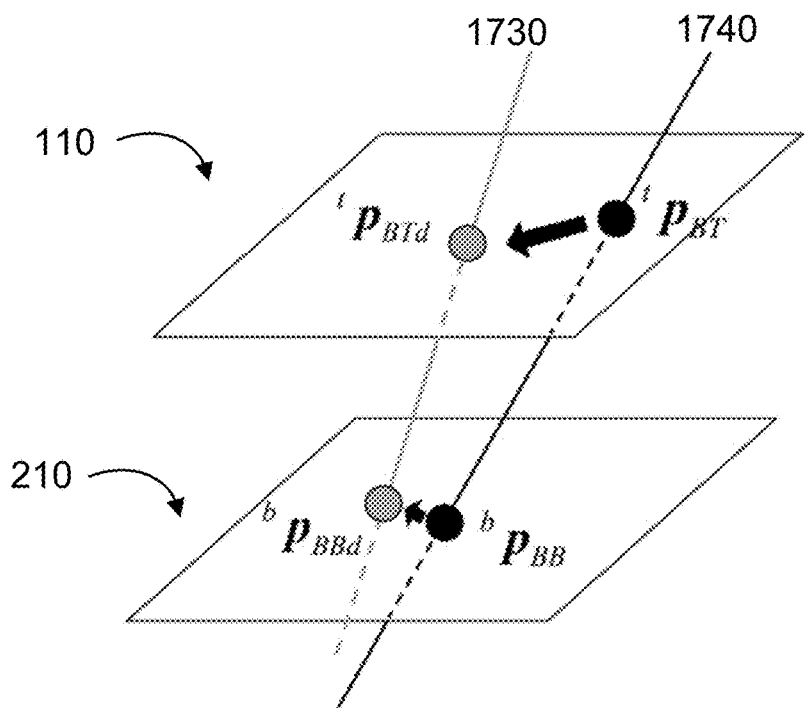
FIG. 17B provides a diagram of kinematics, in accordance with the present disclosure.

Forward kinematics is presented to represent the needle guide position in the absolute coordinate frame using ball joint positions in the planar coordinate frames fixed to individual x-y stages. Let $$ {}_{\square}^{t}p_{BT} = \begin{bmatrix} x_t \\ y_t \end{bmatrix} $$

be the ball position of the top x-y stage with respect to the coordinate frame fixed to it as shown in FIG. 17. FIG. 17 provides AutoSPINe kinematics with FIG. 17A showing parallel plan kinematics including upper fiducial marker (e.g., first fiducial marker 140), lower fiducial marker (e.g., second fiducial marker 240), MRI image planes 1710, top plane (e.g., first planar stage 110), bottom plane (e.g., second planar stage 210) and needle guide 1720 and FIG. 17B showing a needle positioning concept including desired needle position 1730 and current needle position 1740. Similarly, let $$ {}_{\square}^{b}p_{BB} = \begin{bmatrix} x_b \\ y_b \end{bmatrix} $$

be the ball position of the bottom x-y stage. Defining $$_{\square}^{t}P_{BT} = \begin{bmatrix} {}^{t}p_{BT} \\ 1 \end{bmatrix} \text{ and } {}_{\square}^{b}P_{BB} = \begin{bmatrix} {}^{b}p_{BB} \\ 1 \end{bmatrix},$$

homogeneous transformation, ${}^{0}_{\square}P_{BT} = {}^{0}_{\square}T_{t}{}^{t}P_{BT}$ and ${}^{0}_{\square}P^{BB} = {}^{0}_{\square}T_{t}{}^{t}P_{BB}$ provides the ball positions with respect to the base coordinate frame $\Sigma_0$ $\square$ where ${}^{0}_{\square}T_t$ and ${}^{0}_{\square}T_b$ are homogeneous transformation matrices. Note that without the loss of generality, the x-y planes of $\Sigma_t$ $\square$ and $\Sigma_b$ $\square$ can be assumed parallel to each other to simplify the kinematic representation.

C. Measurement of Needle Position Using MRI

Imaging of two fiducial markers attached to the needle guide enables detection of the 4-DOF position and orientation as shown in FIG. 17A. The spherical exterior of the fiducial markers makes their outer diameter appear as circles in the MRI regardless of their orientation image slice. Running a circle detection algorithm on an image slice with the fiducial marker visible returns the location of the fiducial marker in the image. The 4-DOF position and orientation can then be calculated from the location of the two markers. Measurement of ${}^{0}_{\square}P_{FU}$ and ${}^{0}_{\square}P_{FL}$ determines the line along with the needle guide. The intersection between this line and each of the x-y planes of $\Sigma_t$ $\square$ and $\Sigma_b$ $\square$ determines the ball joint position. In FIG. 3B and FIG. 16B (providing an image of fiducials on the cannula), fiducials are placed between the upper and lower stages, while in FIG. 17A they are both placed above the top plane.

D. Image Jacobian and Needle Positioning

Figure 18:
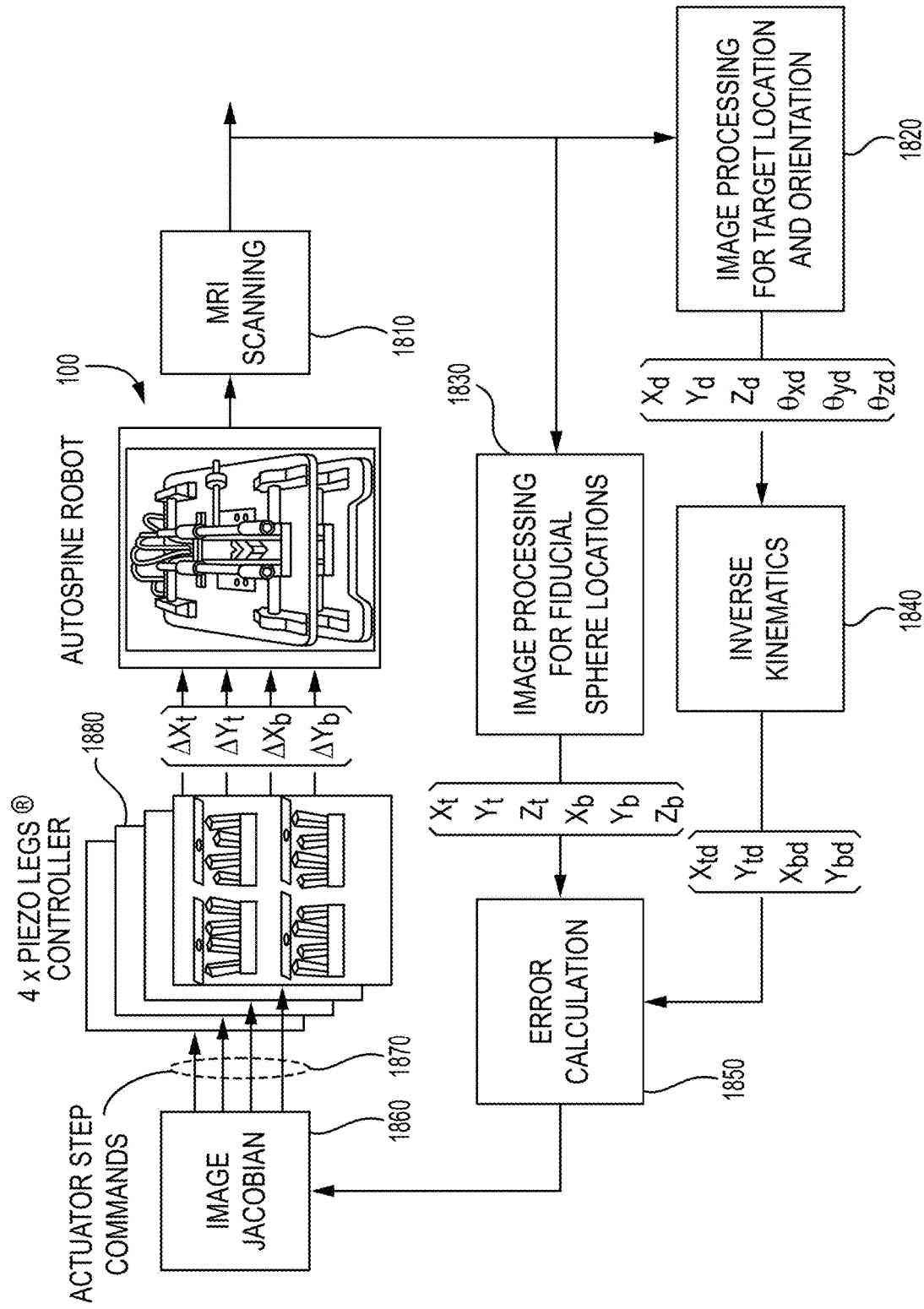
FIG. 18 provides a flow chart illustrating an example method for positioning, in accordance with the present disclosure.

Image Jacobians relate small actuator displacements, $\Delta x_t$, $\Delta y_t$, $\Delta x_b$, $\Delta y_b$, and resultant ball joint displacements expressed in the global coordinate frame, $\Delta^{0}_{\square}P_{BT}$ and $\Delta^{0}_{\square}P_{BB}$. As shown in FIG. 17B, matching ${}^{0}_{\square}P_{BT}$ and ${}^{0}_{\square}P_{BB}$ with the ones of the desired needle position, $\Delta^{0}_{\square}P_{BTd}$ and $\Delta^{0}_{\square}P_{BBd}$, solves the inverse kinematics. Note that the X-Y stages can be operated independently from each other. The solution is unique as long as ${}^{0}_{\square}P_{BT}$ and ${}^{0}_{\square}P_{BB}$ exist, i.e., unless the needle is not completely orthogonal to the parallel planes. In general, image-guided needle positioning is performed in an iterative fashion as illustrated in FIG. 18. FIG. 18 provides an MRI guided needle positioning system diagram and linear motor operation diagram. FIG. 18 provides MIII scanning 1810, image processing for target location and orientation 1820, image processing for fiducial sphere locations 1830, inverse kinematics 1840, error calculation 1850, image jacobian 1860, and actuator step commands 1870, piezo legs controllers 1880, and robot 100.

Visual Robot Navigation with Super-Resolution Mri

A. Concept

SR imaging technique processes multiple images with known sub-pixel spatial shifts, typically introduced by moving the camera or the object of interest in the scene, and reconstructs a new image that has a higher resolution than that of the original images. Usually a super-resolution image is produced by numerically solving a cost optimization problem. When it comes to resolution enhancement of MRI images, there is a technical barrier to introduction of sub-pixel displacements in the target object. This requires highly precise positioning usable in a MRI scanner. Note that given the specific architecture of MRI, moving the image acquisition component is not an option. The FOV of the MRI image can be changed, but is generally only considered to be an effective method in improving the resolution in the through-plane direction.

AutoSPINe operates its needle guide and displaces its fiducial markers within MRI imaging resolution of 1 mm. The sub-pixel MRI images are processed to determine the marker positions beyond MRI resolution and navigate the robot toward the target. The displacements are introduced by operating one or multiple of PIEZO LEG actuators. Forward kinematics computes resultant small displacements in the fiducial markers. Note that this operation must be performed in an open-loop fashion as sub-pixel movements are essentially not visible in MRI. An arbitrary trajectory may be used to acquire a set of raw images as long as the displacements are known.

B. Specific Imaging Procedure

Estimation of Image Jacobian: To compute the image Jacobian three points were used, a central origin point, A 15 mm movement in the x axis, and a 15 mm movement in the y axis. These points were chosen to isolate the x and y actuator movements of the robot if positioned approximately parallel to the image coordinate plane. For the SR and bicubic interpolation (BI) image targeting, we determined that repeating the Jacobian procedure with the larger resolution images yielded the same result as scaling the base resolution Jacobian.

Super resolution offset matrix generation: To determine the spatial shifts for image reconstruction, coordinate points are generated randomly ranging from −1 to 1 pixels. The first point is where the first image is taken and is considered the origin point for the following coordinates. The movement in steps required to reach each of the random points is calculated by subtracting each point from the previous point and multiplying the difference by the inverse of the image Jacobian. The generated shifts will be stored in the offset matrix $M_k$ for each of N images (k=1 . . . N).

Super resolution image construction: The SR image is reconstructed using gradient descent optimization to minimize the error between the base resolution images, $I_k$ (k=1 . . . N), and the current best guess of the high resolution image to iteratively update the best guess of the high resolution image:

$$\hat{X} = \underset{X}{\operatorname{argmin}} \left( \sum_{k=1}^{n} \|D_k B_k M_k X - I_k\|_2^2 \right)$$

where $B_k$ is the blur matrix and $D_k$ is the down-sampling matrix. This reconstruction was performed by an example code based on the IBP algorithm. Stopping criteria is 100 iterations or when mean square error is below 0.01% of the mean square error before optimization.

For the experimental validation presented in this disclosure, four images (N=4) were collected to double the resolution of the original images. FIG. 19 shows the four images acquired with a vector arrow representing the spatial shift applied in each image with respect to the first image. After the 4-th image is taken, the AutoSPINe is returned to the first point and the SR image is reconstructed. FIG. 19 provides an MIII SR reconstruction with FIG. 19A showing a first image with no spatial shift, FIGS. 19B-D showing three spatially shifted images with arrows representing magnitude and direction of the spatial shift relative to the image (with the box representing 1 pixel), and FIG. 19E showing a SR reconstruction.

Marker detection: MATLAB circle finding function, imfindcircles, was used to detect markers in images and MM image slices. The centerpoint position and radius of the markers were retrieved from this method.

Numerical Analysis

First, numerical analysis was conducted in MATLAB to quantify the theoretical impact of SR reconstruction of images on the accuracy of the circle finding algorithm previously described. Bicubic Interpolated images were also compared to evaluate the performance of a single image method of increasing resolution. To simulate the loss of information in the image capturing process, an image of a circle was created at a very high resolution (5000×5000 pixels) with a known center point as the ground truth. To create the low resolution image, a blur was applied, the image was down scaled to match the spatial resolution of an MIll image, and noise was added. This was considered the base resolution image.

Figure 20C:
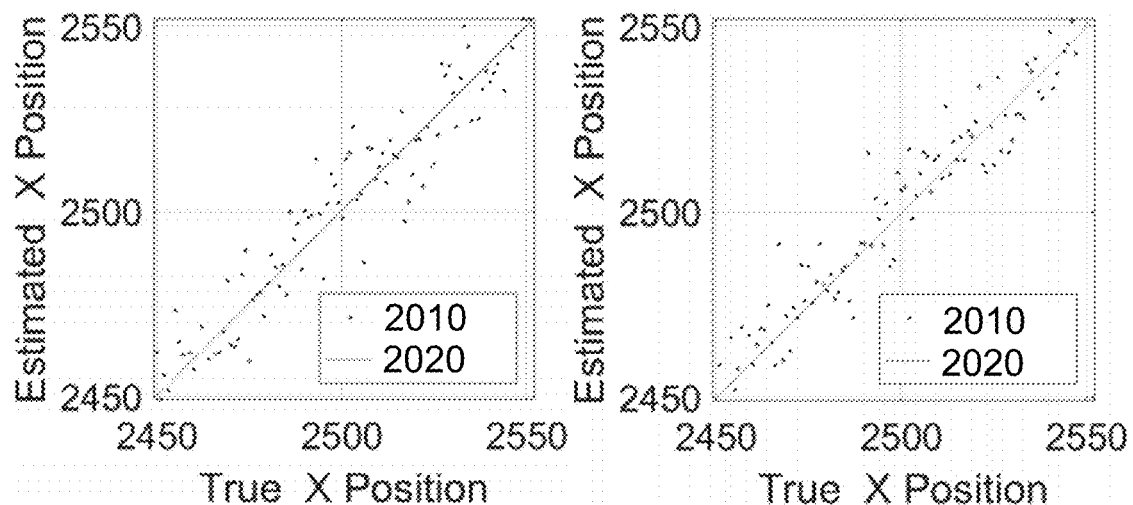
FIG. 20C provides a graph of estimated against true center point positions, in accordance with the present disclosure.
Figure 20C:
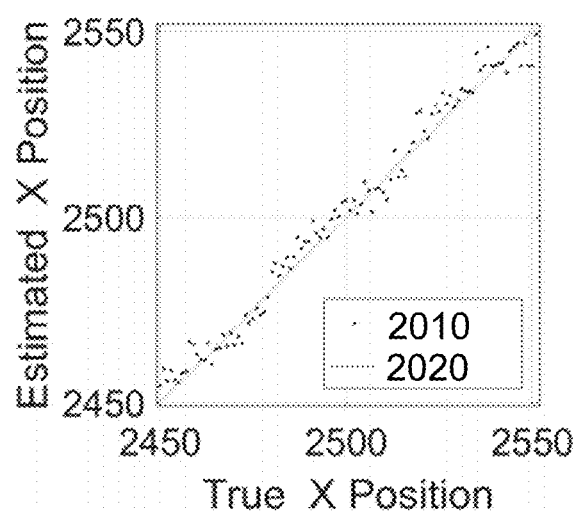

The process outlined in Table I was repeated 100 times and the circle centerpoint coordinates found in the base resolution, interpolated, and SR images were scaled and are plotted against the ground truth centerpoint in FIG. 20. FIG. 20 provides distribution of estimated center point x coordinate plotted against true center point x coordinate (showing data 2010 and ideal line 2020) with FIG. 20A showing base resolution distribution, FIG. 20B showing bicubic interpolation distribution, and FIG. 20C showing SR distribution.

TABLE I

WORKFLOW OF NUMERICAL ANALYSIS

| Step | Description |
|---|---|
| 1 | Create image of very high resolution circle |
| 2 | Apply blur, downscale, and add noise to image |
| 3 | Find center point of circle in generated Base Resolution Image |
| 4 | Use bicubic interpolation to double resolution of Base Image |
| 5 | Find centerpoint of circle in Interpolated Image |
| 6 | Repeat step 1-2 to create 3 shifted Base Resolution Images |
| 7 | Construct SR image from the 4 BR images and find centerpoint |
| 8 | Repeat steps 1-7 with the circle shifted 1 pixel to the right |

The mean error of the base resolution images was 0.156 normalized pixels (percentage of image size). Applying bicubic interpolation yielded a similar mean error of 0.135. The SR images yielded a mean error of 0.066, verifying that reconstructing SR images improves accuracy of object targeting. The improvement from the base resolution images to the SR images, as well as the interpolated images to the SR images was confirmed to be statistically significant with a two-tailed F-test ($p<0.0001$).

Experiments

A. Benchtop Experiments

Figure 21A:
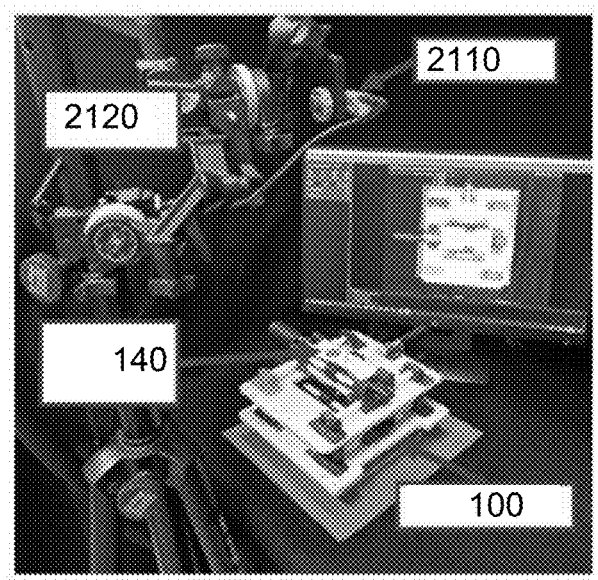
FIG. 21A provides a photo of an experimental setup, in accordance with the present disclosure.
Figure 21B:
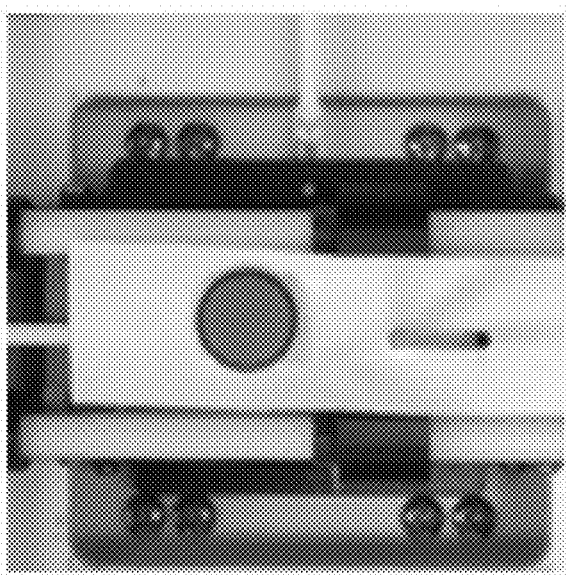
FIG. 21B provides an image acquired from an experiment, in accordance with the present disclosure.
Figure 21C:
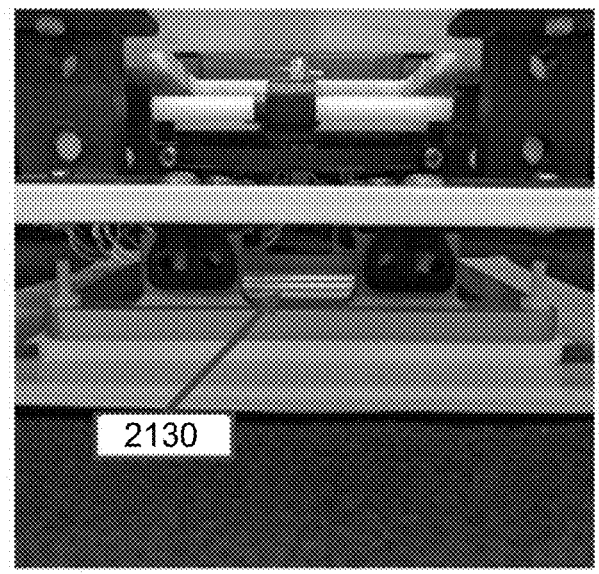
FIG. 21C provides a photo of an experimental setup, in accordance with the present disclosure.
Figure 21D:
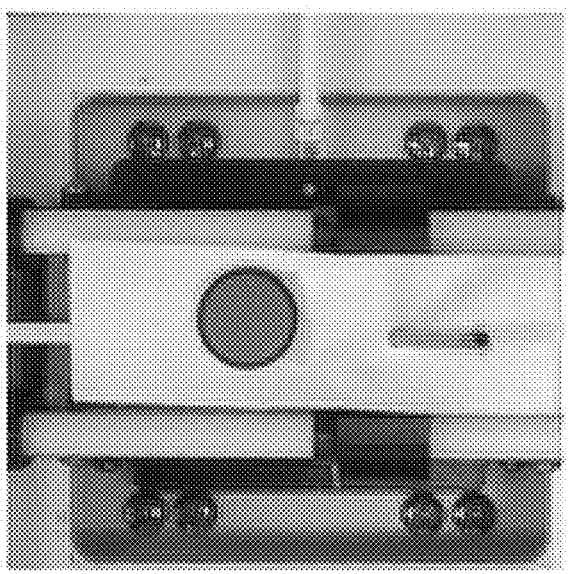
FIG. 21D provides a reconstructed image, in accordance with the present disclosure.

To confirm the findings of our numerical analysis applied to robot control, a set of experiments were designed to measure and compare the precision of needle positioning and injection guided by regular images against guidance by SR reconstructed images. To measure the positioning precision with more fidelity than the images, a sharpened rod was pushed through the cannula to puncture a target mounted below the robot. A flat sheet of paper clamped between an acetal resin plate and an ABS plate was used as the target so the punctures would be visible and the distance between punctures could be measured. The AutoSPINe was attached rigidly on top of the target, as seen in FIG. 21C. FIG. 21 provides a benchtop experimental set up including a camera 2110 and tripod 2120 with FIG. 21B showing base resolution image acquired from experiment, FIG. 21C showing a target 2130 mounted below AutoSPINe, and FIG. 21D showing a Super Resolution image reconstructed from benchtop experiments.

The bottom plane was kept stationary for the experiments to simplify the kinematics of the robot to single plane motion in two axes. This adjustment allows for the replacement of the two fiducials with a red circle printed on a small piece of paper (HP Laserjet 4700dn, 600 dpi) mounted on the top plane. The printed fiducial ensures that there is a clear, flat circle to be found in the images, shown in FIG. 21B. The benchtop (BT) experiments were designed to be repeated in Mill with minimal adjustments, so an RGB Camera (Intel Realsense) was mounted onto a tripod and placed over the robot, mimicking the coronal view in Mill, as seen in FIG. 21A.

The camera used for the benchtop experiment has a native resolution of 640×480 pixels. Spatial resolution was set at 1.5 pixels per mm by placing the camera at a height of 33 cm. The images were downscaled using interpolation to match the spatial resolution of the Mill images which is 1 pixel per mm. The images were also cropped to match the FOV of the Mill, 128×128 pixels. An image acquired from this procedure is shown in FIG. 21B.

Figure 22A:
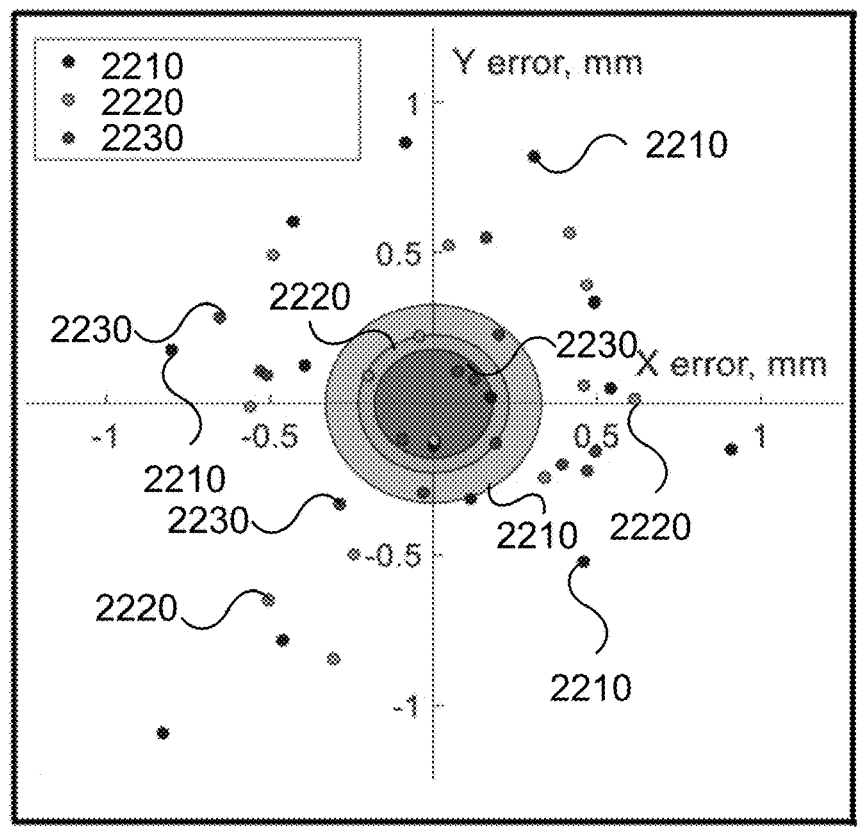
FIG. 22A provides a plot of experimentally measured resolutions, in accordance with the present disclosure.
Figure 22B:
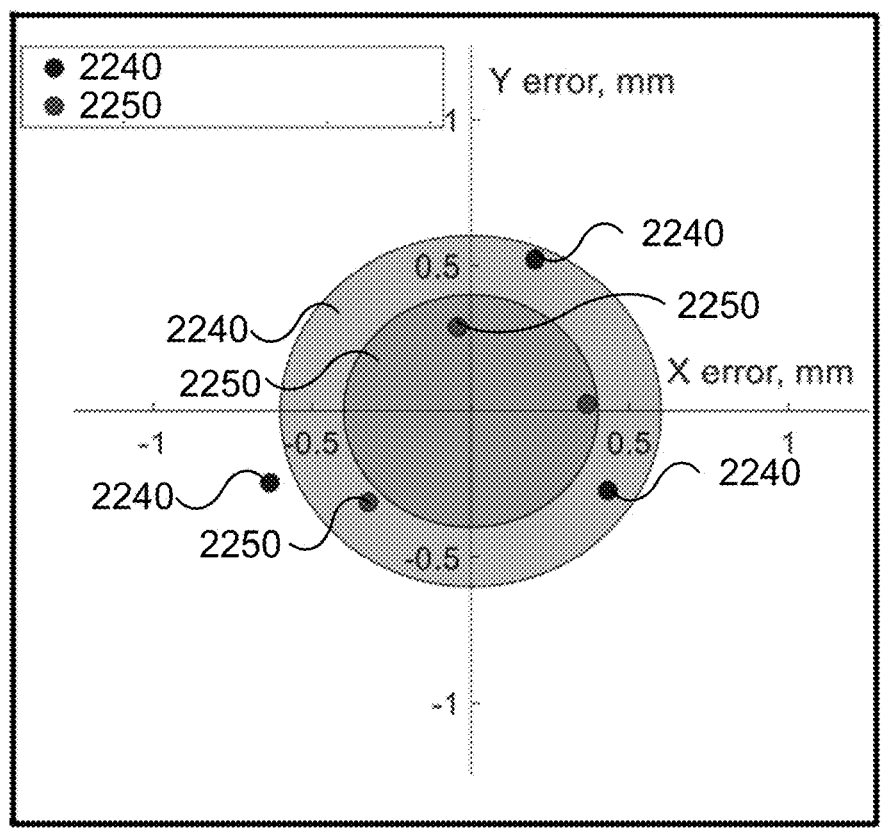
FIG. 22B provides a plot of experimentally measured resolutions, in accordance with the present disclosure.

The experiments were performed as outlined in Table II. The target position is considered to be the position of the fiducial markers when the first puncture in the trial is made. For the bicubic interpolation trial, each image was interpolated to double the resolution and used for targeting and updates. The SR trial also follows the same procedure but for each image taken, the SR image construction procedure described in this disclosure was followed to construct the SR image. An example of an SR image acquired from the benchtop experiments is shown in FIG. 21D. For each trial, the target paper was replaced or moved so the punctures from each trial could be analyzed separately. 14 punctures were made in each trial to compare the positioning repeatability with the RGB camera base resolution, SR method, and Bicubic Interpolation. Each puncture point from the experiments is shown in FIG. 22A. FIG. 22 provides experimental results, base resolution targeting 2210, interpolated targeting 2220 and super resolution targeting 2230, circles represent the standard deviation of each group, with FIG. 22A showing benchtop results and FIG. 22B showing MM results (Mill resolution (1 mm) 2240 and super resolution (0.5 mm) 2250. The distance of each point to the group means were calculated using a stereo microscope.

TABLE II

WORKFLOW OF BENCHTOP AND MRI EXPERIMENTS

| Step | Description |
|---|---|
| 1 | Take image of robot in central position |
| 2 | Move robot and take images to calculate Image Jacobian |
| 3 | Create puncture and take image(s) at target position |
| 4 | Move robot to random point and take image(s) |
| 5 | Calculate error between current and target position |
| 6 | Move robot calculated error and take image(s) |
| 7 | Repeat steps 5-6 until error is less than 1, then create puncture |
| 8 | Repeat Steps 4-7 for desired number of punctures |

A two tailed F-test validates that the variances of the standard and SR groups are statistically different ($p<0.05$). The standard deviations were 0.33 mm and 0.18 mm for the standard and SR targeting groups respectively, with the interpolation-based targeting group producing a 0.23 mm standard deviation. The number of iterations and time needed for each puncture, as well as the puncture precision are summarized in Table III.

TABLE III

RESULTS OF BENCHTOP AND MRI EXPERIMENTS

|  | BT | BT SR | BT BI | MRI | MRI SR |
|---|---|---|---|---|---|
| Number of iterations | 1.08 (0.29) | 1.58 (0.67) | 1.17 (0.39) | 2.00 (1.41) | 1.50 (0.71) |
| Time (min) | 1.08 (0.29) | 4.75 (2.34) | 1.08 (0.29) | 7.00 (5.66) | 26.50 (9.19) |
| Puncture precision (mm) | (0.33) | (0.18) | (0.23) | (0.60) | (0.40) |

Mean (STD). Precision of needle puncture was evaluated by STD.

B. MRI Experiments

The MRI experiments were performed similarly to the benchtop experiments, with scanner bore 2310 and the AutoSPINe (e.g., robot 100) secured rigidly (with straps 2320) onto the scanner bed as shown in FIG. 23A. The fiducial marker 140 used for the MRI experiments is shown in FIG. 23B, mounted on the top stage of the AutoSPINe since only two DOF positioning is considered for the experiments. Only one slice of the MRI images was used to calculate the centerpoint of the fiducial in that plane. A Processed SR image with detected circle overlaid on image is shown in FIG. 23C. FIG. 23 provides an MM set up with FIG. 23B showing fiducial marker attached to top plane of robot and FIG. 23C showing a super resolution image reconstructed from MM experiments with a circle plotted based on image finding algorithm.

Three punctures were made in the base resolution experiment and the SR experiment. Experimental positioning results are shown in FIG. 22B. Scanner time restrictions precluded collection of a statistically significant sample size, however, the standard deviation of the SR group was 33% smaller than that of the MRI resolution group, 0.60 mm vs. 0.40 mm. The number of iterations and time needed for each puncture are also summarized in Table III.

Discussion

A. Positioning Performance

This work's primary focus is the utility of SR image reconstruction in the positioning of a robot in the MRI environment. The experimental results detailed in FIG. 22 clearly demonstrate that SR image reconstruction produces more repeatable positioning of the robot. The MRI results follow the trend shown in benchtop experiments. The results also indicate that the use of bicubic interpolation to "scale up" a single image for targeting improves performance as well, but not as much as the full SR image reconstruction.

There is an important difference in the variance of the MRI and benchtop experiments, this is likely due to the lower native resolution of the MM, and the impact of this lower resolution on the precision of the iterative positioning method. Although the images used in the benchtop experiments were scaled to match the spatial resolution of the MRI images, since interpolation was used to downscale the images, they still provide a more accurate image of the fiducial marker. This performance improvement is important to the utility of precision MRI positioning robots, as MRI resolution has been a limiting factor in positioning performance.

B. Imaging Time Cost for Precision

Although a significant increase in positioning repeatability was found due to the SR based robot navigation method described, this comes with the necessity of increased imaging time. Because the robot used relies on an iterative image feedback method for positioning control, it is likely not necessary to implement the SR reconstruction at each iteration in order to realize a performance improvement. A more efficient scheme would be to do initial positioning in the MM native resolution, only performing the SR procedure once the robot's positioning is coincident with the target at the precision of the MM. In other words, SR reconstruction is only necessary once the robot has reached the limit of the MM resolution.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A method of controlling a robot comprising:
   performing a cycle comprising:
      receiving, by a controller, more than one MRI image from an MRI machine, the MRI image comprising a position of one or more fiducial markers of a surgical tool;
      merging the MRI images, wherein the MRI images are spatially shifted MRI images, and wherein each of the MRI images is spatially shifted by a known amount by displacing, via one or more actuators of the robot, the one or more fiducial markers of the surgical tool by a known amount;
      estimating an enhanced resolution image comprising the position of the one or more fiducial markers of the surgical tool, based, at least in part, on the merged MRI images;
      determining a fiducial position error based, at least in part, on the position of the one or more fiducial markers of the surgical tool in the enhanced resolution image and target fiducial coordinates indicative of a desired position of the one or more fiducial markers; and
      moving, by the one or more actuators of the robot, the surgical tool to a position based, at least in part, on the determined fiducial position error.

2. The method of claim 1, wherein the cycle further comprises:

determining if the position of the one or more fiducial markers of the surgical tool in the enhanced resolution image is coincident with the target fiducial coordinates.

3. The method of claim 1, wherein the moving is based, at least in part, on visual servoing.

4. The method of claim 1, wherein the robot comprises:
a first planar stage comprising:
   a first joint configured to receive the surgical tool; and
   a first mechanism configured to move the surgical tool; and
a second planar stage comprising:
   a second joint configured to receive the surgical tool; and
   a second mechanism configured to move the surgical tool;
wherein the second planar stage is generally parallel with the first planar stage; and
wherein the surgical tool comprises a cannula configured to extend through the first and second joints.

5. The method of claim 4, wherein the surgical tool further comprises a needle configured to be inserted into the cannula.

6. The method of claim 5 further comprising:
controlling a depth of the needle into a patient.

7. The method of claim 4, wherein the one or more fiducial markers comprise an MRI-visible substance; and
wherein the one or more fiducial markers are symmetrical and coaxial with a line between the first joint and the second joint.

8. A method of controlling a robot comprising:
receiving, by a controller, target fiducial coordinates indicative of a desired position of one or more fiducial markers of a surgical tool;
performing a cycle comprising:
   receiving, by a controller, more than one MRI image from an MRI machine, each MRI image comprising a respective position of the one or more fiducial markers of the surgical tool;
   merging the MRI images, wherein the MRI images are spatially shifted MRI images, and wherein each of the MRI images is spatially shifted by a known amount by displacing, via one or more actuators of the robot, the one or more fiducial markers of the surgical tool by a known amount;
   estimating an enhanced resolution image comprising the position of the one or more fiducial markers of the surgical tool, based, at least in part, on the merged MRI images;
   determining a fiducial position error based, at least in part, on the respective positions of the one or more fiducial markers of the surgical tool in the enhanced resolution image and the target fiducial coordinates;
   moving, by the one or more actuators of the robot, the surgical tool to a position based, at least in part, on the fiducial position error; and
   determining if the respective positions of the one or more fiducial markers of the surgical tool in the enhanced resolution image are coincident with the target fiducial coordinates; and
if the respective positions of the one or more fiducial markers of the surgical tool are not coincident with the target fiducial coordinates, repeating performing the cycle until the respective positions of the one or more fiducial markers of the surgical tool are coincident with the target fiducial coordinates.

9. The method of claim 1, wherein the enhanced resolution image has a higher resolution than a resolution of each of the MRI images.

10. The method of claim 1, wherein the enhanced resolution image has a higher resolution than a highest resolution that the MRI machine is capable of capturing.

11. The method of claim 8, wherein the enhanced resolution image has a higher resolution than a resolution of each of the MRI images.

12. The method of claim 8, wherein the enhanced resolution image has a higher resolution than a highest resolution that the MRI machine is capable of capturing.

* * * * *